US007449293B2

(12) United States Patent
Leighton et al.

(10) Patent No.: US 7,449,293 B2
(45) Date of Patent: Nov. 11, 2008

(54) **METHODS AND COMPOSITIONS FOR DETECTING *BACILLUS* SPECIES**

(75) Inventors: Terrance Leighton, Oakland, CA (US); Kijeong Kim, Oakland, CA (US)

(73) Assignee: Children's Hospital & Research Center at Oakland, Oakland, CA (US)

(*) Notice: Subject to any disclaimer, the term of this patent is extended or adjusted under 35 U.S.C. 154(b) by 355 days.

(21) Appl. No.: 10/949,472

(22) Filed: Sep. 24, 2004

(65) Prior Publication Data

US 2005/0202460 A1 Sep. 15, 2005

Related U.S. Application Data

(60) Provisional application No. 60/506,197, filed on Sep. 26, 2003.

(51) Int. Cl.

*C12Q 1/68* (2006.01)
*C12P 19/34* (2006.01)
*C07H 21/04* (2006.01)

(52) U.S. Cl. ........................ 435/6; 435/91.2; 536/24.33

(58) Field of Classification Search ....................... None
See application file for complete search history.

(56) References Cited

U.S. PATENT DOCUMENTS

| | | | | |
|---|---|---|---|---|
| 6,448,016 | B1 | 9/2002 | Rastogi | |
| 6,472,155 | B1 * | 10/2002 | McKinney | 435/6 |
| 2003/0082563 | A1 | 5/2003 | Bell | |
| 2003/0203362 | A1 * | 10/2003 | Hunter-Cevera et al. | 435/6 |

OTHER PUBLICATIONS

El-Helow, E.R. Identification and molecular characterization of a novel *Bacillus* strain capable of degrading Tween-80. FEMS Microbiology Letters (2001) 196: 119-122.*

Hoffmaster et al. Evaluation and validation of a real-time polymerase chain reaction assay for rapid identification of *Bacillus anthracis*. Emerging Infectious Diseases. (2002) 8(10): 1178-1182.*

Buck et al. Design strategies and performance of custom DNA sequencing primers. BioTechniques (1999) 27(3): 528-536.*

Anderson et al., Identification of a Region of Genetic Variability Among *Bacillus anthracis* Strains and Related Species, J. Bacteriol. 178: 377-384 (1996).

Jackson et al, PCR Analysis of Tissue Samples From the 1979 Sverdlovsk Anthrax Victims: The Presence of Multiple *Bacillus anthracis* Strains in Different Victims, Proc. Natl. Acad. Sci, 95: 1224-9 (1998).

Patra et al., Isolation of a Specific Chromosomic DNA Sequence of *Bacillus anthracis* and its Possible Use in Diagnosis, FEMS Microbiol. 15: 223-231 (1996).

Ruhfel et al, Interspecies Transduction of Plasmids Among *Bacillus anthracis, B. cereus*, and *B. thuringiensis*, J. Bact., 157: 708-11 (1984).

* cited by examiner

*Primary Examiner*—Kenneth R. Horlick
*Assistant Examiner*—Angela Bertagna
(74) *Attorney, Agent, or Firm*—James S. Keddie; Bozicevic, Field & Francis LLP

(57) ABSTRACT

The invention provides methods and compositions for rapid, sensitive, and highly specific nucleic acid-based detection of *B. anthracis* in a sample. In general, the methods involve detecting within the sspE gene of *B. anthracis* the presence of a fragment of six unique contiguous nucleotides that is not present in the sspE genes of other *Bacillus* bacteria or other non-*Bacillus* bacteria. In many embodiments, the methods involve amplifying a nucleic acid comprising at least a fragment of an sspE gene from a sample, and detecting the presence of the six unique contiguous nucleotide fragments in the nucleic acid. The invention also provides primers and kits for detection of *B. anthracis* in a sample. The subject invention finds use in a variety of different applications, including research, medical, diagnostic and military applications.

6 Claims, 11 Drawing Sheets

| | 1 10 20 30 40 50 60 70 | |
|---|---|---|
| Ba ATCC 14578$^T$ | GGAGGTGAGAAAGATGAGTAAAAAACAACAAGGTTATAACAAGGCAACTTCTGGTGCTAGCATTCAAAGCACA | (SEQ ID NO:11) |
| | Ssp1F1 | |
| Bc ATCC 14579$^T$ | .....................................................................T... | (SEQ ID NO:37) |
| Bt DSM 2046$^T$ | ............................................................T........T... | (SEQ ID NO:38) |
| Bt BGSC 4BG1 | .....................................................................T... | (SEQ ID NO:39) |
| Bt BGSC 4BG1* | .................AC.................C..T..............C........C.....T... | (SEQ ID NO:40) |
| Bt BGSC 4AW1 | ..........................................A..........................T... | (SEQ ID NO:41) |
| Bm ATCC 6462$^T$ | .......................................T.............................T... | (SEQ ID NO:42) |
| Bw DSM 11821$^T$ | .......................................T.............................T... | (SEQ ID NO:43) |
| Bm ATCC 10206 | ..........................................A..........................T... | (SEQ ID NO:44) |
| Bp DSM 12442$^T$ | ................................C.........A..........................T... | (SEQ ID NO:45) |

| | 80 90 100 110 120 130 140 | |
|---|---|---|
| Ba ATCC 14578$^T$ | AATGCTAGTTATGGTACAGAGTTTGCGACTGAAACAAATGTACAAGCAGTAAAACAAGCAAACGCACAATCAG | (SEQ ID NO:11) |
| | Ssp1F2 | |
| Bc ATCC 14579$^T$ | ....................A.....T.............................................. | (SEQ ID NO:37) |
| Bt DSM 2046$^T$ | ..........................A.............................................. | (SEQ ID NO:38) |
| Bt BGSC 4BG1 | ........................T.A.........G....G............................... | (SEQ ID NO:39) |
| Bt BGSC 4BG1* | ........C...........A..C..A................................G..T...A..G... | (SEQ ID NO:40) |
| Bt BGSC 4AW1 | .......................C..A.............C................................ | (SEQ ID NO:41) |
| Bm ATCC 6462$^T$ | ........C.................A........G.......................G............. | (SEQ ID NO:42) |
| Bw DSM 11821$^T$ | ........C.................A........G.......................G............. | (SEQ ID NO:43) |
| Bm ATCC 10206 | ........C.................A.....G........................CA...T.......... | (SEQ ID NO:44) |
| Bp DSM 12442$^T$ | ........C.................A.....G........................CA...T.......... | (SEQ ID NO:45) |

| | Ssp1R1/R2<br>150 160 170 180 190 200 210 220 | |
|---|---|---|
| Ba ATCC 14578$^T$ | AAGCTAAGAAAGCGCAAGCTTCTGGTGCTAGCATTCAAAGCACAAATGCTAGTTATGGTACAGAATTTGCAAC | (SEQ ID NO:11) |
| | Ssp1F3 | |
| Bc ATCC 14579$^T$ | ....A........A..............A------.....TG....C.......................... | (SEQ ID NO:37) |
| Bt DSM 2046$^T$ | ....A........A..............A------.....TG....C.......................... | (SEQ ID NO:38) |
| Bt BGSC 4BG1 | ....G........A..............A------.....TG............................... | (SEQ ID NO:39) |
| Bt BGSC 4BG1* | ....AC.......C........A.....A------.....TG..........C..............C..... | (SEQ ID NO:40) |
| Bt BGSC 4AW1 | ....A........A........C.....A------.....TG....C.......................... | (SEQ ID NO:41) |
| Bm ATCC 6462$^T$ | .G..AC.......A..........C....------.....TG......................G........ | (SEQ ID NO:42) |
| Bw DSM 11821$^T$ | .G..AC.......A..........C....------.....TG......................G........ | (SEQ ID NO:43) |
| Bm ATCC 10206 | ....G..A.....A..G......A.C...G.TG.......TG..........C..C..C.....G........ | (SEQ ID NO:44) |
| Bp DSM 12442$^T$ | ....G..A.....A..G......A.C...G.TG.......TG..........C..C..C.....G........ | (SEQ ID NO:45) |

FIG. 1 1/2

```
                          230       240       250       260       270       280       290
Ba ATCC 14578T   TGAAACAGACGTGCATGCTGTGAAAAAACAAAATGCACAATCAGCTGCAAAACAATCACAATCTTCTAG--TT(SEQ ID NO:11)
                                                               Ssp1R3
Bc ATCC 14579T   ....................................TA.G.............................--C.(SEQ ID NO:37)
Bt DSM 2046T     ....................................TA.G.............................--..(SEQ ID NO:38)
Bt BGSC 4BG1     ................................................G....................--..(SEQ ID NO:39)
Bt BGSC 4BG1*    .......A.T..A..A..A......C..GCG.........G...AG...C.GA..G.C...G....AG.TGCA(SEQ ID NO:40)
Bt BGSC 4AW1     .........T.....C.........C..GC..C...........AA.....GA..G.....A.....G.TGCA(SEQ ID NO:41)
Bm ATCC 6462T    .........T........A..................................................--..(SEQ ID NO:42)
Bw DSM 11821T    .........T........A..................................................--..(SEQ ID NO:43)
Bm ATCC 10206    ...C.....T.....A..A......C..................A......A.................--CA(SEQ ID NO:44)
Bp DSM 12442T    ...C.....T.....A..A......C..................A......A.................--CA(SEQ ID NO:45)

                       300         310       320       330       340       350       360
Ba ATCC 14578T   CAAATCAGTAA--------------------------------------------------------------(SEQ ID NO:11)

Bc ATCC 14579T   ...........--------------------------------------------------------------(SEQ ID NO:37)
Bt DSM 2046T     ....CG.....--------------------------------------------------------------(SEQ ID NO:38)
Bt BGSC 4BG1     ...........--------------------------------------------------------------(SEQ ID NO:39)
Bt BGSC 4BG1*    ....GTGCA..TGCTAGCTATGGTACAGAATTTGCAACTGAAACAGATGTACATGCAGTGAAAAAACAAAATG(SEQ ID NO:40)
Bt BGSC 4AW1     ....GTGCA..CGCTAGTTATGGTACAGAATTTGCAACTGAAACAGATGTGCATGCTGTGAAAAAACAAAATG(SEQ ID NO:41)
Bm ATCC 6462T    ....CG.....--------------------------------------------------------------(SEQ ID NO:42)
Bw DSM 11821T    ....CG.....--------------------------------------------------------------(SEQ ID NO:43)
Bm ATCC 10206    .G.....A...--------------------------------------------------------------(SEQ ID NO:44)
Bp DSM 12442T    .G.....A...--------------------------------------------------------------(SEQ ID NO:45)

                     370       380       390       400       410
Ba ATCC 14578T   -----------------------------------------------

Bc ATCC 14579T   -----------------------------------------------
Bt DSM 2046T     -----------------------------------------------
Bt BGSC 4BG1     -----------------------------------------------
Bt BGSC 4BG1*    CACAATCAGCTGCAAAAAAATCACAATCTTCTAGCTCTAATCAATAA(SEQ ID NO:40)
Bt BGSC 4AW1     CACAATCAGCTGCAAAACAATCACAATCTTCTAGTTCAAATCAGTAA(SEQ ID NO:41)
Bm ATCC 6462T    -----------------------------------------------
Bw DSM 11821T    -----------------------------------------------
Bm ATCC 10206    -----------------------------------------------
Bp DSM 12442T    -----------------------------------------------
```

FIG. 1 2/2

GCTTCTGGTGCTagcatt (SEQ ID NO:14)

CTTCTGGTGCTagcattC (SEQ ID NO:15)

TTCTGGTGCTagcattCA (SEQ ID NO:16)

TCTGGTGCTagcattCAA (SEQ ID NO:17)

CTGGTGCTagcattCAAA (SEQ ID NO:18)

TGGTGCTagcattCAAAG (SEQ ID NO:19)

GGTGCTagcattCAAAGC (SEQ ID NO:20)

GTGCTagcattCAAAGCA (SEQ ID NO:21)

TGCTagcattCAAAGCAC (SEQ ID NO:22)

GCTagcattCAAAGCACA (SEQ ID NO:23)

CTagcattCAAAGCACAA (SEQ ID NO:24)

TagcattCAAAGCACAAA (SEQ ID NO:25)

agcattCAAAGCACAAAG (SEQ ID NO:26)

AGCTTCTGGTGCTagcat (SEQ ID NO:27)

AAGCTTCTGGTGCTagca (SEQ ID NO:28)

CAAGCTTCTGGTGCTagc (SEQ ID NO:29)

GCAAGCTTCTGGTGCTag (SEQ ID NO:30)

CGCAAGCTTCTGGTGCTa (SEQ ID NO:31)

catttgtgctttgaatgc (SEQ ID NO:32)

gcatttgtgctttgaatg (SEQ ID NO:33)

agcatttgtgctttgaat (SEQ ID NO:34)

tagcatttgtgctttgaa (SEQ ID NO:35)

ctagcatttgtgctttga (SEQ ID NO:36)

FIG. 6

SEQUENCE LISTING

```
<160> NUMBER OF SEQ ID NOS: 36

<210> SEQ ID NO 1
<211> LENGTH: 25
<212> TYPE: DNA
<213> ORGANISM: Bacillus anthracis

<400> SEQUENCE: 1

gagaaagatg agtaaaaaac aacaa                                           25


<210> SEQ ID NO 2
<211> LENGTH: 21
<212> TYPE: DNA
<213> ORGANISM: Bacillus anthracis

<400> SEQUENCE: 2

catttgtgct ttgaatgcta g                                               21


<210> SEQ ID NO 3
<211> LENGTH: 21
<212> TYPE: DNA
<213> ORGANISM: Bacillus anthracis

<400> SEQUENCE: 3

cagagtttgc gactgaaaca a                                               21


<210> SEQ ID NO 4
<211> LENGTH: 21
<212> TYPE: DNA
<213> ORGANISM: Bacillus anthracis

<400> SEQUENCE: 4

catttgtgct ttgaatgcta g                                               21
```

-continued

<210> SEQ ID NO 5
<211> LENGTH: 21
<212> TYPE: DNA
<213> ORGANISM: Bacillus anthracis

<400> SEQUENCE: 5
cttctggtgc tagcattcaa a 21

<210> SEQ ID NO 6
<211> LENGTH: 21
<212> TYPE: DNA
<213> ORGANISM: Bacillus anthracis

<400> SEQUENCE: 6
attgtgattg ttttgcagct g 21

<210> SEQ ID NO 7
<211> LENGTH: 24
<212> TYPE: DNA
<213> ORGANISM: Bacillus anthracis

<400> SEQUENCE: 7
tgaacccgta cttgtaatcc aatc 24

<210> SEQ ID NO 8
<211> LENGTH: 23
<212> TYPE: DNA
<213> ORGANISM: Bacillus anthracis

<400> SEQUENCE: 8
atcgctccag tgttgatagt gct 23

<210> SEQ ID NO 9
<211> LENGTH: 24
<212> TYPE: DNA
<213> ORGANISM: Bacillus anthracis

<400> SEQUENCE: 9
gttgtacctg gttatttagc actc 24

<210> SEQ ID NO 10
<211> LENGTH: 24
<212> TYPE: DNA
<213> ORGANISM: Bacillus anthracis

<400> SEQUENCE: 10
accacttaac aaaattgtag ttcc 24

<210> SEQ ID NO 11
<211> LENGTH: 301
<212> TYPE: DNA
<213> ORGANISM: Bacillus anthracis

<400> SEQUENCE: 11
ggaggtgaga aagatgagta aaaaacaaca aggttataac aaggcaactt ctggtgctag 60
cattcaaagc acaaatgcta gttatggtac agagtttgcg actgaaacaa atgtacaagc 120
agtaaaacaa gcaaacgcac aatcagaagc taagaaagcg caagcttctg gtgctagcat 180
tcaaagcaca aatgctagtt atggtacaga atttgcaact gaaacagacg tgcatgctgt 240
gaaaaaacaa aatgcacaat cagctgcaaa acaatcacaa tcttctagtt caaatcagta 300
a 301

-continued

<210> SEQ ID NO 12
<211> LENGTH: 6
<212> TYPE: DNA
<213> ORGANISM: Bacillus anthracis

<400> SEQUENCE: 12 agcatt 6

<210> SEQ ID NO 13
<211> LENGTH: 17
<212> TYPE: DNA
<213> ORGANISM: Bacillus anthracis

<400> SEQUENCE: 13
ggtgctagca ttcaaag 17

<210> SEQ ID NO 14
<211> LENGTH: 18
<212> TYPE: DNA
<213> ORGANISM: Bacillus anthracis

<400> SEQUENCE: 14
gcttctggtg ctagcatt 18

<210> SEQ ID NO 15
<211> LENGTH: 18
<212> TYPE: DNA
<213> ORGANISM: Bacillus anthracis

<400> SEQUENCE: 15
cttctggtgc tagcattc 18

<210> SEQ ID NO 16
<211> LENGTH: 18
<212> TYPE: DNA
<213> ORGANISM: Bacillus anthracis

<400> SEQUENCE: 16
ttctggtgct agcattca 18

<210> SEQ ID NO 17
<211> LENGTH: 18
<212> TYPE: DNA
<213> ORGANISM: Bacillus anthracis

<400> SEQUENCE: 17
tctggtgcta gcattcaa 18

<210> SEQ ID NO 18
<211> LENGTH: 18
<212> TYPE: DNA
<213> ORGANISM: Bacillus anthracis

<400> SEQUENCE: 18
ctggtgctag cattcaaa 18

<210> SEQ ID NO 19
<211> LENGTH: 18
<212> TYPE: DNA
<213> ORGANISM: Bacillus anthracis

<400> SEQUENCE: 19
tggtgctagc attcaaag 18

-continued

<210> SEQ ID NO 20
<211> LENGTH: 18
<212> TYPE: DNA
<213> ORGANISM: Bacillus anthracis

<400> SEQUENCE: 20
ggtgctagca ttcaaagc 18

<210> SEQ ID NO 21
<211> LENGTH: 18
<212> TYPE: DNA
<213> ORGANISM: Bacillus anthracis

<400> SEQUENCE: 21
gtgctagcat tcaaagca 18

<210> SEQ ID NO 22
<211> LENGTH: 18
<212> TYPE: DNA
<213> ORGANISM: Bacillus anthracis

<400> SEQUENCE: 22
tgctagcatt caaagcac 18

<210> SEQ ID NO 23
<211> LENGTH: 18
<212> TYPE: DNA
<213> ORGANISM: Bacillus anthracis

<400> SEQUENCE: 23
gctagcattc aaagcaca 18

<210> SEQ ID NO 24
<211> LENGTH: 18
<212> TYPE: DNA
<213> ORGANISM: Bacillus anthracis

<400> SEQUENCE: 24
ctagcattca aagcacaa 18

<210> SEQ ID NO 25
<211> LENGTH: 18
<212> TYPE: DNA
<213> ORGANISM: Bacillus anthracis

<400> SEQUENCE: 25
tagcattcaa agcacaaa 18

<210> SEQ ID NO 26
<211> LENGTH: 18
<212> TYPE: DNA
<213> ORGANISM: Bacillus anthracis

<400> SEQUENCE: 26
agcattcaaa gcacaaag 18

<210> SEQ ID NO 27
<211> LENGTH: 18
<212> TYPE: DNA
<213> ORGANISM: Bacillus anthracis

<400> SEQUENCE: 27

-continued agcttctggt gctagcat 18

<210> SEQ ID NO 28
<211> LENGTH: 18
<212> TYPE: DNA
<213> ORGANISM: Bacillus anthracis

<400> SEQUENCE: 28
aagcttctgg tgctagca 18

<210> SEQ ID NO 29
<211> LENGTH: 18
<212> TYPE: DNA
<213> ORGANISM: Bacillus anthracis

<400> SEQUENCE: 29
caagcttctg gtgctagc 18

<210> SEQ ID NO 30
<211> LENGTH: 18
<212> TYPE: DNA
<213> ORGANISM: Bacillus anthracis

<400> SEQUENCE: 30
gcaagcttct ggtgctag 18

<210> SEQ ID NO 31
<211> LENGTH: 18
<212> TYPE: DNA
<213> ORGANISM: Bacillus anthracis

<400> SEQUENCE: 31
cgcaagcttc tggtgcta 18

<210> SEQ ID NO 32
<211> LENGTH: 18
<212> TYPE: DNA
<213> ORGANISM: Bacillus anthracis

<400> SEQUENCE: 32
catttgtgct ttgaatgc 18

<210> SEQ ID NO 33
<211> LENGTH: 18
<212> TYPE: DNA
<213> ORGANISM: Bacillus anthracis

<400> SEQUENCE: 33
gcatttgtgc tttgaatg 18

<210> SEQ ID NO 34
<211> LENGTH: 18
<212> TYPE: DNA
<213> ORGANISM: Bacillus anthracis

<400> SEQUENCE: 34
agcatttgtg ctttgaat 18

<210> SEQ ID NO 35
<211> LENGTH: 18
<212> TYPE: DNA
<213> ORGANISM: Bacillus anthracis

<400> SEQUENCE: 35

-continued

```
tagcatttgt gctttgaa                                                    18


<210> SEQ ID NO 36
<211> LENGTH: 18
<212> TYPE: DNA
<213> ORGANISM: Bacillus anthracis

<400> SEQUENCE: 36

ctagcatttg tgctttga                                                    18
```

METHODS AND COMPOSITIONS FOR DETECTING *BACILLUS* SPECIES

FIELD OF THE INVENTION

The invention relates to detection of *Bacillus* bacteria, especially bacteria of the species *B. anthracis.*

BACKGROUND OF THE INVENTION

Anthrax infections are initiated by endospores of *B. anthracis*, a Gram-positive soil organism. Anthrax endospores do not divide, have no measurable metabolism, and are resistant to drying, heat, ultraviolet light, gamma radiation, and many disinfectants. In some types of soil, anthrax spores can remain dormant for decades. All known anthrax virulence genes are expressed by vegetative cells of *B. anthracis* that result from the germination of spores within the body. Endospores introduced into the body by abrasion, inhalation, or ingestion are phagocytosed by macrophages and carried to regional lymph nodes. Endospores germinate inside the macrophages and become vegetative bacteria; the vegetative bacteria are then released from the macrophages, multiply in the lymphatic system, and enter the bloodstream until there are as many as $10^7$ to $10^8$ organisms/ml of blood, causing massive septicemia. Once they have been released from the macrophages, there is no evidence that an immune response is initiated against vegetative bacilli. Anthrax bacilli express virulence factors, including toxin and capsule polypeptides. The resulting toxemia and bacterimia have systemic effects that lead to death of the host.

The major virulence factors of *B. anthracis* are encoded on two virulence plasmids, pX01 and pX02. The toxin-bearing plasmid, pX01, is 184.5 kilobases (Kb) in size and codes for the genes that produce the secreted exotoxins. The toxin gene complex is composed of protective antigen (PA), lethal factor (lef), and edema factor (EF). The three exotoxin components combine to form two binary toxins. Edema toxin consists of EF, which is a calmodulin-dependent adenylate cyclase, and PA, the binding moiety that permits entry of the toxin into the host cell. Increased cellular levels of cyclic AMP interfere with water homeostasis and are believed to be responsible for the massive edema seen in cutaneous anthrax. Edema toxin inhibits neutrophil function in vitro and neutrophil function is impaired in patients with cutaneous anthrax infection. Lethal toxin consists of LF, which is a zinc metalloprotease that inactivates mitogen-activated-protein kinase kinase in vitro, and PA, which acts as the binding domain. Lethal toxin stimulates macrophages to release tumor necrosis factor $\alpha$ and interleukin 1$\beta$, which are partly responsible for sudden death in systemic anthrax. The capsule-bearing plasmid, pX02, is 95.3 Kb in size and codes for three genes (capB, capC, and capA) involved in the synthesis of the polyglutamyl capsule.

The exotoxins are thought to inhibit the immune response mounted against infection, whereas the capsule inhibits phagocytosis of vegetative anthrax bacilli. The expression of all known major virulence factors is regulated by host-specific factors such as elevated temperature (>37° C.) and carbon dioxide concentration (>5%) and by the presence of serum components. Both plasmids are required for full virulence and the loss of either results in an attenuated strain. Historically, bacterial strains used for anthrax vaccines were made by rendering virulent strains free of one or both plasmids. By way of example, 'Pasteur' is an avirulent pX02-carrying strain that is encapsulated but does not express exotoxin components, while 'Sterne' is an attenuated strain that carries pX01 and can synthesize exotoxin components but does not have a capsule.

There is currently a need for reliable and rapid detection methods for anthrax bacteria. A nucleic acid based assay would be of particular interest since it could be readily adapted to high-throughput and in-field applications. Fully virulent or vaccine strains of *B. anthracis* can be easily identified by their virulence plasmid composition, however, many *B. anthracis* strains do not contain these plasmids, e.g., fully attenuated *B. anthracis* strains, and, as such, cannot be detected by such methods. Also, specific detection of the *B. anthracis* chromosome has been difficult due to its close phylogenetic relationship to other members of the *B. cereus* group. There have been many attempts to develop chromosomal detection assays for *B. anthracis*, however they are not reliable because they do not adequately distinguish *B. anthracis* from other *Bacillus* species in the *B. cereus* clade. In addition, *B. anthracis* virulence plasmids may be transferred to near neighbor *B. cereus* clade species, resulting in derivatives with unconventional virulence and genetic compositions which would not be distinguished by existing assays.

Accordingly, there is a need for rapid and reliable DNA-based assays for detecting anthrax and related *Bacillus* spp. This invention meets this need, and others.

Literature

Literature of interest includes: U.S. Patent publication 20030082563, U.S. Pat. No. 6,448,016 and Jackson et al, Proc. Natl. Acad. Sci, 95: 1224-9 (1998), Ruhfel et al, J. Bact., 157: 708-11 (1984), Patra et al., FEMS Microbiol. 15: 223-231 (1996), and Anderson et al., J. Bacteriol. 178: 377-384 (1996).

SUMMARY OF THE INVENTION

The invention provides methods and compositions for rapid, sensitive, and highly specific nucleic acid-based (e.g., DNA based) detection of *B. anthracis* in a sample. In general, the methods involve detecting within the sspE gene of *B. anthracis* the presence of a fragment of six contiguous nucleotides of unique sequence that is not present in the sspE genes of other *Bacillus* bacteria or other non-*Bacillus* bacteria. In many embodiments, the methods involve amplifying a nucleic acid comprising at least a fragment of an sspE gene from a sample, and detecting the presence of the unique six contiguous nucleotide fragments in the nucleic acid. The invention also provides primers and kits for detection of *B. anthracis* in a sample. The invention additionally provides primers and methods for discriminating *B. anthracis* and near-neighbor chromosomes from each other and those of phylogenetically unrelated bacteria. The subject invention finds use in a variety of different applications, including research, medical, diagnostic and military applications.

BRIEF DESCRIPTION OF THE DRAWINGS

FIG. 1 shows an alignment of the nucleotide sequences corresponding to sspE genes of various representative *Bacillus* species using Clustal W. The sequence of the sspE gene of Ba ATCC 14578, Bc ATCC $14579^T$, Bt DSM 20461, Bt BGSC 4BG1, Bt BGSC 4BG1*, Bt BGSC 4AW1, Bm ATCC $6462^T$, Bw DSM $11821^T$, Bm ATCC 10206 and Bp DSM $12442^T$, as shown in this figure, is provided in the sequence listing as SEQ ID NO:11, SEQ ID NO:37, SEQ ID NO:38, SEQ ID NO:39, SEQ ID NO:40, SEQ ID NO:41, SEQ ID NO:42, SEQ ID NO:43, SEQ ID NO:44 and SEQ ID NO:45 respectively.

FIG. 6 shows the sequences of exemplary detection primers of the present invention.

DEFINITIONS

Figure 2:
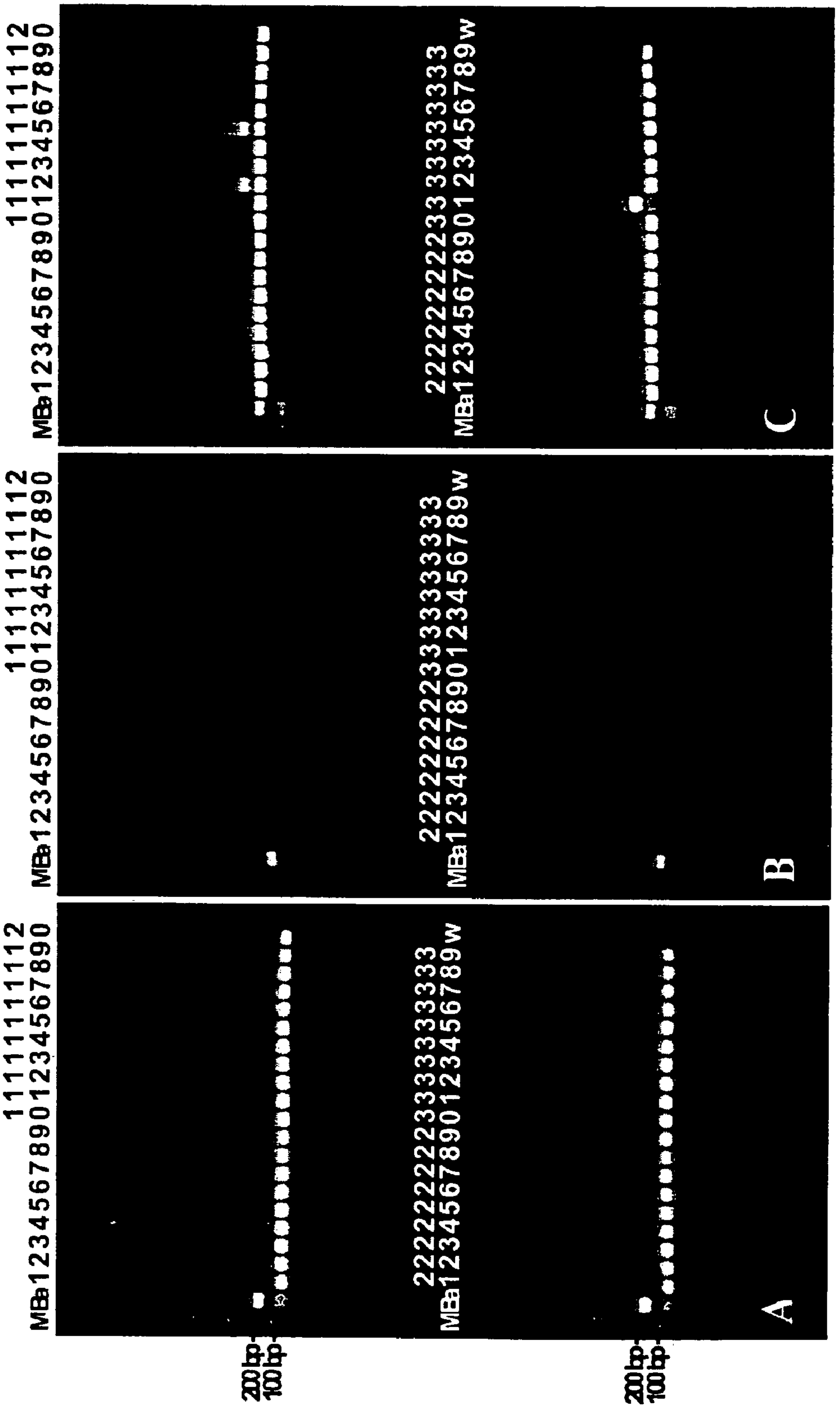
FIG. 2 is a composite figure showing three gel photographs A, B and C. The figure displays the results of sspE PCR assays with three sets of primers and genomic DNA from 40 representative sspE genotypes from the *B. cereus* group.

As used herein, the terms "determining," "measuring," and "assessing," and "assaying" are used interchangeably and include both quantitative and qualitative determinations.

The term "nucleic acid" as used herein means a polymer composed of nucleotides, e.g., deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "nucleoside" and "nucleotide" are intended to include those moieties that contain not only the known purine and pyrimidine base moieties, but also other heterocyclic base moieties that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The terms "ribonucleic acid" and "RNA" as used herein refer to a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length. Oligonucleotides may be made synthetically or by copying a template (e.g., an SspE gene template) using a polymerase.

The term "polynucleotide" as used herein refers to a single or double stranded polymer composed of nucleotide monomers, of generally greater than 100 nucleotides in length.

The term "stringent conditions" refers to conditions under which a primer will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes on an array surface between complementary binding members, e.g., between probes and complementary targets in a sample, e.g., duplexes of nucleic acid probes, such as DNA probes, and their corresponding nucleic acid targets that are present in the sample, e.g., their corresponding mRNA analytes present in the sample. A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mnM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a probe. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary" under the invention, and in most situations two sequences are sufficiently complementary when at least about 85% (preferably at least about 90%, and most preferably at least about 95%) of the nucleotides share base pair organization over a defined length of the molecule.

As used herein, a "biological sample" refers to a sample of tissue or fluid isolated from a subject, which in the context of the invention generally refers to samples suspected of containing nucleic acid and/or cellular particles of human *B. anthracis*, which samples, after optional processing, can be analyzed in an in vitro assay. Typical samples of interest include, but are not necessarily limited to, respiratory secretions (e.g., samples obtained from fluids or tissue of nasal passages, lung, and the like), blood, plasma, serum, blood cells, fecal matter, urine, tears, saliva, milk, organs, biopsies, and secretions of the intestinal and respiratory tracts. Samples also include samples of in vitro cell culture constituents including but not limited to conditioned media resulting from the growth of cells and tissues in culture medium, e.g., recombinant cells, and cell components.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to a "oligonucleotide primer" includes a plurality of such primers and reference to "primer" includes reference to one or more the primers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The invention provides methods and compositions for rapid, sensitive, and highly specific nucleic acid-based detection of *B. anthracis* in a sample. In general, the methods involve detecting within the sspE gene of *B. anthracis* the presence of a unique sequence fragment of six contiguous nucleotides that is not present in the sspE genes other *Bacillus* bacteria or other non-*Bacillus* bacteria. In many embodiments, the methods involve amplifying a nucleic acid comprising at least a fragment of an sspE gene from a sample, and detecting the presence of the six contiguous unique nucleotide fragments in the nucleic acid. The invention also provides primers and kits for detection of *B. anthracis* in a sample. The subject invention finds use in a variety of different applications, including research, medical, diagnostic, security screening, and military applications.

The invention is based on the discovery of a 6-bp *B. anthracis* specific insert sequence in a highly conserved spore structural gene (sspE). As such, in one embodiment, the invention provides a novel PCR-based assay for the detection of a *Bacillus anthracis* chromosomal gene. Several primers are described herein and may be used in a PCR assays. Some primers enable detection and discrimination of *B. anthracis* and members of the *B. cereus* group simultaneously, while other primers enable the second primer set allowed PCR detection of *B. anthracis* exclusively. No false positives were obtained in using this assay to investigate a total of 272 strains representing a broad range of *B. anthracis* near- and distant-neighbor species. Previously reported PCR assays such as those involving Ba813, gyrB, rpoB, SG-749 RFLP and multi-locus VNTR, had significant levels of false positive responses. A multiplex PCR assay using the first set of primers discriminated among all forms of fully attenuated, vaccine and fully virulent *B. anthracis* strains, members of the *Bacillus cereus* group, other *Bacillus* spp. and non-*Bacillus* bacteria. In addition, a real-time PCR assay has been developed which can rapidly discriminated among all forms of fully attenuated, vaccine and fully virulent *B. anthracis* strains, and members of the *Bacillus cereus* group. The specificity and simplicity of these assays facilitate rapid, reliable and inexpensive assays for detection of *B. anthracis* and other *B. cereus* group chromosomes.

Primers and Probes for Detection of *B. anthracis*

The detection methods described herein rely on detection of a region of six contiguous nucleotides of the genomic sspE gene of *B. anthracis*, corresponding to nucleotides 176-181 of SEQ ID NO: 11 or complement thereof, that is not present in the sspE genes of other bacteria, including other bacteria of the genus *Bacillus*. This sequence, i.e., AGCATT, is referenced herein as the "*B. anthracis* sspE insert sequence", and is set forth in SEQ ID NO: 12. The *B. anthracis* sspE insert sequence may be detected using a variety of methods that will be described in greater detail below. In general, these methods may be either amplification-based methods (i.e., methods in which the presences of a nucleic acid amplification product indicates the presence or absence of the *B. anthracis* sspE insert sequence) or hybridization-based methods (i.e., methods in which the presence of the *B. anthracis* sspE insert sequence is identified by hybridization of a probe to that sequence).

As such, the invention provides an oligonucleotide primer for detection of the *B. anthracis* sspE insert sequence. This primer is termed a "detection primer" and may be used alone, or in compositions with other primers to detect the aforementioned *B. anthracis* sspE insert sequence. In certain embodiments the detection primer is present in the absence of other primers and may be used in, for example, a primer extension reaction or, in alternative embodiments, the detection primer may be paired with a second primer to form a primer pair, i.e., a "detection primer pair", that is suitable for use in, for example, an amplification reaction such as the polymerase chain reaction (PCR), for the detection of the *B. anthracis* sspE insert sequence. A detection primer may hybridize to a sspE sequence of *B. anthracis* (by virtue of its binding to a *B. anthracis* sspE insert sequence) but not to sspE sequences from other *Bacillus* species (e.g., *B. cereus*).

As such, the detection primer is usually based on the sequence of the *B. anthracis* sspE gene, and usually is complementary to and binds to the *B. anthracis* sspE gene, or its complement, at a region corresponding to the *B. anthracis* sspE insert sequence.

In certain embodiments, a detection primer comprises the *B. anthracis* sspE insert sequence, or its complement, at a position that is 0, 1, 2, 3, 4 or 5 or more, usually up to about 10 nucleotides from the 3' end of the primer. FIG. 6 shows examples of these detection primers (SEQ ID NOS:14-26), in which the *B. anthracis* sspE insert sequence is underlined. The complements of these exemplary primers may also be used in the subject methods.

In certain other embodiments, the 3' end of the detection primer ends in the *B. anthracis* sspE insert sequence, or its complement. FIG. 6 shows examples of these detection primers (SEQ ID NOS:27-36), in which the *B. anthracis* sspE insert sequence (which is only partially represented in each of the primers) is underlined.

In many embodiments, therefore, a detection primer contains at least 8 contiguous nucleotides (i.e., 9, 10, 11, 12, 13, 14, 15, 16 or 17 contiguous nucleotides) of any one of the sequences set forth in SEQ ID NOS:14-39 or their complements. The at least 8 contiguous nucleotides may lie at the 3' end of any of the sequences of the sequences set forth in SEQ ID NOS:14-39 or their complements. In other embodiments, a detection primer comprises any of the sequences set forth in SEQ ID NOS:14-39, or their complements.

As mentioned above, a detection primer may be present in a composition with at least one other primer. In some embodiments, these primers provide for amplification of a nucleic acid product (an "amplicon") when used in conjunction with a detection primer in an amplification reaction in the presence of a nucleic acid template containing the *B. anthracis* sspE gene. As such, in most embodiments, the primers provide for amplification of an amplicon containing at least a fragment of the sspE gene of *B. anthracis*. At least one other primer, therefore, usually binds to a region of the *B. anthracis* genome that is proximal to the *B. anthracis* sspE insert sequence, i.e., is separated from the *B. anthracis* sspE insert sequence by more than about 20 contiguous nucleotides (i.e., more than about 50, more than about 100, more than about 200, more than about 300, more than about 500, more than about 1000, more than about 1500 contiguous nucleotides) and up to about 2000 contiguous nucleotides. As such, at least one other primer may bind to a region in the *B. anthracis* sspE gene and, as such, may have at least 8 contiguous nucleotides (i.e., about 10, about 15, about 20, usually up to about 50 contiguous nucleotides) of SEQ ID NO:11 or complement thereof. SEQ ID NOS: 1, 3 and 6 represent examples of these primers.

The subject detection primer may also be present in a composition with primers for detection of other sequences, such as the pXO1 or pXO2 plasmids of *B. anthracis*, or any other set of primers for detection of *B. anthracis, B. cereus* clade members or determination of their virulence.

In general, primers, including the detection primers and other oligonucleotide primers discussed herein, are usually at least about 8, at least about 10, at least about 12, at least about 15, at least about 20, at least about 25, at least about 30, at least about 35 or at least about 40, usually up to about 50 or about 80 nucleotides in length. In most embodiments, a primer binds to a target nucleic acid such that nucleic acid synthesis is initiated from the 3' end of the nucleic acid by a suitable enzyme, such as a DNA polymerase. As is known in the art, primers may be labeled with, for example, a fluorescent or a radioactive label to facilitate detection of an amplified nucleic acid. In particular embodiments, primers are labeled for detection by real-time PCR instrumentation.

In particular embodiments, therefore, a subject oligonucleotide may contain 8 contiguous nucleotides of any of SEQ ID NO:2, 4, 5 or 14-36, or any complements thereof, which 8 contiguous nucleotides may be at the 3' end of the oligonucleotide. In other embodiments, the oligonucleotide may have the sequence of SEQ ID NOS:2, 4 or 5, or any complement thereof, SEQ ID NO:14-36, or any complement thereof. A subject oligonucleotide may have the sequence set forth in SEQ ID NO:12, or complement thereof.

Methods of Detection

The invention provides DNA-based assays for detecting *Bacillus* species in a sample, and assays for specifically detecting *B. anthracis* in a sample. The methods discriminate between *B. anthracis* and other phylogenetically related members of the *Bacillus* genus. In general, the method involves amplifying nucleic acids from a sample. If a diagnostic nucleic acid product is obtained, the presence of a

*Bacillus* species in a sample is indicated. Exemplary methods involve amplifying a nucleic acid from a sample using a detection primer and at least one other primer, as described above, and assessing the amplified nucleic acids. These exemplary methods are highly sensitive, and may detect as few as 1 colony forming units (e.g., less than 2 cfu, less than about 5 cfu, less than about 10 cfu, less than about 20 cfu, less than about 50 cfu, less than about 100 cfu, less than about 200 cfu, or less than about 1000 cfu) of *Bacillus* bacteria (or genome equivalent thereof) in a single microliter of sample.

As is known in the art, an amplified nucleic acid may be assessed by a number of methods, including, for example, determining the presence or absence of the nucleic acid, determining the size of the nucleic acid, determining the thermal melting temperature of the nucleic acid product or determining the abundance of a nucleic acid in relation to another amplified nucleic acid. In most embodiments, an amplified nucleic acid is assessed using gel electrophoresis, nucleic acid hybridization, sequencing, and/or detection of a signal from a label bound to the amplified nucleic acid. Methods of amplifying (e.g., by polymerase chain reaction) nucleic acid, methods of performing primers extension, and methods of assessing nucleic acids are generally well known in the art (e.g., see Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.) and need not be described in any great detail.

The subject assays may be readily performed using primer extension methods using, for example, differentially labeled nucleotides in a primer extension mix. However, in general, methods that employ nucleic acid amplification, e.g. PCR, are preferred.

The invention provides methods of detecting bacteria of the genus *Bacillus*, including *Bacillus anthracis* in a sample. In general, the methods involve amplifying a nucleic acid product from a sample using a detection primer and a second primer that binds to the *B. anthracis* genome at a position, as discussed above, that is proximal to the *B. anthracis* sspE insert sequence. In most embodiments, the presence, absence, size or thermal melting temperature of particular amplification products is assessed to provide a diagnostic for the presence of *Bacillus* bacteria in a sample.

In certain embodiments, particularly those in which the second primer binds to a region that is at least about 100 nucleotides 5' of the *B. anthracis* sspE insert sequence (for example, the first 90 nucleotides of the *B. anthracis* sspE gene, as set forth in SEQ ID NO:1), two amplification products may be obtained due to a repeated region in the sspE sequence. Since the repeated region is approximately 117 nucleotides (e.g. 115-120 nucleotides) from the *B. anthracis* sspE insert sequence, the amplification products obtained from such an amplification reaction usually differ in size by about 117 nucleotides. In these embodiments, the larger of the two amplification products is only amplified if *B. anthracis* is present in a sample, and, as such, it indicates the presence of *B. anthracis* in a sample. As such, if two amplification products are obtained, and the larger of the products is about 1-17 bp longer than the smaller product, *B. anthracis* is usually present in the sample. In this assay, a product is only amplified if a bacteria of the genus *Bacillus* is present, and, as such, a single amplification product, (corresponding to the smaller of the two bands if *B. anthracis* is present in a sample) indicates the that *Bacillus* bacteria are present in the sample. In these embodiments, amplification products are obtained only if the sample contains bacteria of the genus *Bacillus*, and no amplification products are obtained if no bacteria of the genus *Bacillus* are in the sample. As such, the subject methods provide a method of determining if a sample contains nucleic acid from *Bacillus* spp., and provides a method of specifically detecting *B. anthracis* in a sample.

In other embodiments, particularly those in which the second primer binds to a region that is less than about 100 nucleotides 5' of the *B. anthracis* sspE insert sequence (for example, the first 90 nucleotides of the *B. anthracis* sspE gene, as set forth in SEQ ID NO:1), a single amplification product may be obtained. In these embodiments, if a single amplification product is obtained, *B. anthracis* is usually present in the sample. As such, the subject methods provide a method of determining if a sample contains *Bacillus anthracis*.

In certain other embodiments, particularly those in which the second primer binds to a region that is 3' of the *B. anthracis* sspE insert sequence, amplification products will only be obtained if a species of *Bacillus* bacteria is present in a sample. As such the presence of a *Bacillus* bacterium in the sample is indicated by the amplification product. In these embodiments, if *B. anthracis* is present in a sample, then two amplification products are obtained that differ in size by approximately 117 nucleotides. The smaller of these amplification products is only obtained if *B. anthracis* nucleic acids are present in the sample.

As would be understood by one of skill in the art, the subject methods may be used with nested primers, particular primers that lie outside the region amplified by the detection and second primers, used in the amplification methods described above.

As briefly mentioned above, the subject methods may also be used to assess the virulence of *B. anthracis* in a sample by combining a first pair of primers comprising a detection primer and a second primer for amplification of at least a fragment of a *Bacillus* sspE gene, with one or more sets of virulence plasmid detection primers, which may include primers for detection of virulence plasmids or other virulence determinants, e.g. the *B. anthracis* pXO1 or pXO2 plasmids. Such detection and virulence primer pairs may be used in the same or different reactions.

The subject methods find use for detecting bacteria of the genus *Bacillus*, particularly for detecting *B. anthracis*, in a sample. The sample may be one or a mixture a variety of samples obtained from an individual or from the environment that can be used in a diagnostic or monitoring assay. Samples may be environmental samples (e.g., soil, air, water, the surface of an object), or biological (e.g., blood and other liquid samples of biological origin, solid tissue samples such as a biopsy specimen such as skin, or tissue cultures or cells derived there from and the progeny thereof). Samples may also have been manipulated in any way after their procurement, such as by culture, treatment with reagents, solubilization, or enrichment for certain components, such as polynucleotides. A sample encompasses any sample that has been isolated from a site suspected of being in contact with anthrax or other *Bacillus* bacteria, may contain anthrax spores or a vegetative bacteria, or extract thereof, made from those cells or spores.

In certain embodiments, the subject methods may be performed using "real-time" PCR. Such PCR methods are well known in the art, and may be performed using a Cepheid (Sunnyvale, Calif.) SMARTCYCLER™, ABI (Foster City, Calif.) PRISM 7700 ™, or a Stratagene (La Jolla, Calif.) Mx3000P™ system, or the like. Methods and kits for performing real-time PCR, including multiplex PCR methodologies, may be found with the literature that accompanies the above-referenced systems, or may be obtained from several supply companies, such as Epicenter (Madison, WO), MJ Research (Waltham, Mass.), Qiagen (Valencia Calif.), Roche Applied Science (Indianapolis, Ind.), Stratagene (La Jolla, Calif.) and Promega (Madison, Wis.) and the like.

In alternative embodiments, the *B. anthracis* sspE insert sequence may be detected in a sample by hybridizing a nucleic acid probe containing the *B. anthracis* sspE insert sequence (usually an oligonucleotide probe containing the *B. anthracis* sspE insert sequence) to a sample under stringent hybridization conditions. In one exemplary embodiment, oligonucleotide primers for amplifying at least a portion of the *B. anthracis* sspE gene are employed to amplify a sspE gene nucleic acid fragment from a sample. That fragment may then be contacted with an oligonucleotide probe containing the *B. anthracis* sspE insert sequence under stringent hybridization conditions. Binding of the probe to the fragment indicates the presence of *B. anthracis* in the sample whereas and no significant binding of the probe to the fragment indicates that *B. anthracis* is not present in the sample. As would be recognized by one of skill in the art, a probe may be labeled, e.g., linked to optical detectable (e.g., fluorescent) moiety, to facilitate its detection and increase sensitivity of the assay. The nucleic acid fragment may be linked to a solid support in these methods.

It recognized that nucleic acid sequences complementary to those explicitly recited in this disclosure may be readily employed in the subject methods.

Kits

Kits for use in connection with the subject invention are also provided. Such kits usually include a detection primer, as described above. In certain kits, the detection primer may be present with other primers suitable to provide a detection primer pair for amplifying at least a fragment of the *B. anthracis* sspE gene. The kits may optionally further include virulence detection primers, such as a virulence plasmid detection pair, e.g., primers for the pXO1 or pXO2 plasmids of *B. anthracis*, as discussed above. Kits may also contain instructions for using the kit to detect *B. anthracis* bacteria in a sample using the methods described above, including the above discussed PCR and primer extension methods. Also included in the subject kits may be buffers, dNTPs, and controls, (e.g., positive and negative control nucleic acids) for performing the subject methods. Primers in the subject kits may be detectably labeled or unlabeled.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In particular embodiments, the subject kits include labeled primers and, optionally instructions, for performing the subject methods on real-time PCR instrumentation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Materials and Methods

Bacterial strains: A total of 272 bacterial strains were included in this study. Most strains were obtained from culture collections and type strains of most species were included. *B. cereus* (n=13), *B. thuringiensis* (n=132), *B. mycoides* (n=8), *B. weihenstephanensis* (n=1), *B. pseudomycoides* (n=1), other known *Bacillus* spp. (n=64), unknown *Bacillus* spp. (n=22), and non-*Bacillus* bacteria (n=17) were used.

Polymerase Chain Reaction (PCR): Three sets of primers were designed using OLIGO® primer analysis software (MBI Inc., CO, USA) so that one of the primers in each set contains the *B. anthracis*-specific insertion sequence (see FIG. 1 at approximately position 180; Table 1 provides the primer sequences). Each PCR reaction mixture was prepared in a 50-ml volume, containing 100 ng of template DNA, 0.5 mM of each primers, 200 mM dNTPs, 5 ml of 10× buffer (Qiagen Inc., Valencia, Calif., USA) with 1.5 mM $MgCl_2$ and 2 U of Taq DNA polymerase (Qiagen). The amplification was carried out in a 96-well GeneAmp® PCR system 9700 (Applied Biosystems, Foster City, Calif., USA) with the following parameters: an initial denaturation at 94° C. for 5 min followed by 35 cycles consisting of denaturation at 94° C. for 30 s, annealing at the optimal temperature of each primer pair (Table 1; 54° C. or 56° C.) for 30 s, extension at 72° C. for 30 s, and a final extension at 72° C. for 7 min. 10 ml of the reaction mixtures were subjected to agarose gel electrophoresis. For the multiplex PCR to simultaneously detect two virulence plasmids as well as the chromosome of *B. anthracis*, additional primers targeting the virulence plasmids were designed using PrimerSelect® sequence analysis software (DNASTAR Inc., Madison, Wis., USA). For chromosomal detection, the aforementioned sspE-F1 and sspE-R1 primers were included (Table 2). PCR was carried out in 25-ul reaction volume, with the same conditions as described above except with 2 U of Platimun Taq (Invitrogen), 100 ng of template DNA, 56° C. annealing and 65° C. extension temperature.

Primers: as shown in FIG. 1 and in Table 1 below, three sets of primer based on the sspE gene of *B. anthracis* were designed to amplify *B. anthracis* specific PCR products (the primer positions are indicated with arrows in FIG. 1). One of the primers of each pair is targeted to a *B. anthracis* specific sequence of the sspE gene (sspE-F3, sspE-R1 and sspE-R2). These primer sequences are also found within a repeat sequence upstream. The sspE gene of *B. thuringiensis* BGSC 4AW1 and a second copy of the sspE gene of BGSC 4BG1(*) contain a long insert sequence that is repeated (double underlined) at the C-terminal portion of sspE where the sspE-R3 primer sequence is targeted. Dots indicate nucleotides identical to those of *B. anthracis* and dashes, gaps. Strain designations: Ba, *B. anthracis*; Bc, *B. cereus*; Bt, *B. thuringiensis*; Bm, *B. mycoides*; Bw, *B. weihenstephanensis*; Bp, *B. pseudomycoides*. * represents a second copy of the SspE gene.

All other species did not produce any visible amplicon. (C) PCR of samples with sspE-F3/R3. *B. anthracis* samples yielded two products, a major 234-bp amplicon and a minor 117-bp amplicon that was specific for *B. anthracis*. All other species produced a 234-bp product except for *B. thuringiensis* BGSC 4BG1 (lane 12) and *B. thuringiensis* BGSC 4N1 (lane 15). These two strains produced a 339-bp amplicon in addition to the 234-bp amplicon. *B. thuringiensis* BGSC 4AW1 (lane 31) produced a 339-bp amplicon instead of the 234-bp amplicon. Lanes M, 100-bp DNA size ladder; lane Ba, *B. anthracis* UM23C1-1; lane 1 to 39, *B. cereus* BGSC 6A1, *B. thuringiensis* BGSC 4AZ1, 4I2, 4L1, 4BD1, 4H1, 4B2, 4AH1, *B. cereus* BGSC 6E1, *B. thuringiensis* BGSC 4CD1, 4BH1, 4BG1, 4Y1, *Bacillus* spp. PT030101-02, *B. thuringiensis* BGSC 4N1, *B. cereus* BGSC 6A3, *B. thuringiensis* BGSC 4H2, *B. cereus* ATCC 14579T, *B. thuringiensis* BGSC 4AM1, 4BN1, 4BC1, 4AY1, 4BK1, 4AJ1, 4Z1, 4AN1, 4V1, 4BB1, 4O1, 4AD1, 4AW1, 4BL1, 4K3, *B. mycoides* ATCC 19647, 6462T, 23258, 21929, 10206 and *B. pseudomycoides* DSM 12442T; lane W, negative control (no template DNA).

TABLE 1

Nucleotide sequences of three sets of pcr primers based on the sspE gene of *B. anthracis*

| Primer set | Primers | Products (bp) | Sequence (5'→3') | $T_m$(° C.) | $T_m$(° C.)[a] |
|---|---|---|---|---|---|
| 1 | sspE-F1 | **188**, 71 | GAGAAAGATGAGTAAAAAACAACAA | 59.3 | 56 |
| | sspE-R1 | | CATTTGTGCTTTGAATGCTAG | 59.9 | |
| 2 | sspE-F2 | **105** | CAGAGTTTGCGACTGAAACAA | 63.0 | 54 |
| | sspE-R2 | | CATTTGTGCTTTGAATGCTAG | 59.9 | |
| 3 | sspE-F3 | 234, **117** | CTTCTGGTGCTAGCATTCAAA | 61.9 | 56 |
| | sspE-R3 | | ATTGTGATTGTTTTGCAGCTG | 62.6 | |

Boldface: *B. anthracis*-specific amplicon
[a]Optimised annealing temperature

The sequences of the primers show in Table 1 are provided in the sequence listing as follows: SspE-F1: SEQ ID NO:1; SspE-R1: SEQ ID NO:2: SspE-F2: SEQ ID NO:3, SspE-R2: SEQ ID NO:4; SspE-F3: SEQ ID NO:5; and SspE-R3: SEQ ID NO:6.

TABLE 2

Nucleotide sequences of multiplex pcr primers

| Locus | Primers | Products (bp) | Sequence (5'→3') | $T_m$(° C.) | $T_m$(°C.)[a] |
|---|---|---|---|---|---|
| Lef (pXO1) | lef4-F | **475** | TGAACCCGTACTTGTAATCCAATC | 64.6 | 60 |
| | lef4-R | | ATCGCTCCAGTGTTGATAGTGCT | 66.0 | |
| Cap(C) | cap29-F | **318** | GTTGTACCTGGTTATTTAGCACTC | 59.6 | 56 |
| (pXO2) | cap29-R | | ACCACTTAACAAAATTGTAGTTCC | 59.0 | |
| sspE | sspE-F1 | **188**, 71 | GAGAAAGATGAGTAAAAAACAACAA | 59.3 | 56 |
| (chrsomal) | sspE-R1 | | CATTTGTGCTTTGAATGCTAG | 59.9 | |

Boldface: *B. anthacis*-specific amplicon
[a]Optimized annealing temperature

The sequences of the primers show in Table 2 are provided in the sequence listing as follows: lef4-F: SEQ ID NO:7; lef4-R: SEQ ID NO:8: cap29-F: SEQ ID NO:9, sspE-F1: SEQ ID NO:10; sspE-F 1: SEQ ID NO:1; and sspE-R1: SEQ ID NO:2.

Results

PCR assays results are shown in FIGS. 2-5 and in tables 3 and 4.

FIG. 2 displays the results of sspE PCR assays with three sets of primers and genomic DNA from 40 representative sspE genotypes from the *B. cereus* group. (A) PCR of samples with sspE-F1/R1 primers. *B. anthracis* samples produced two amplicons, a major 188-bp product that was specific for *B. anthracis* and a minor 71-bp product. All other species showed a major 71-bp product only. (B) PCR of samples with sspE-F2/R2. Only *B. anthracis* produced a 105-bp amplicon.

Figure 3:
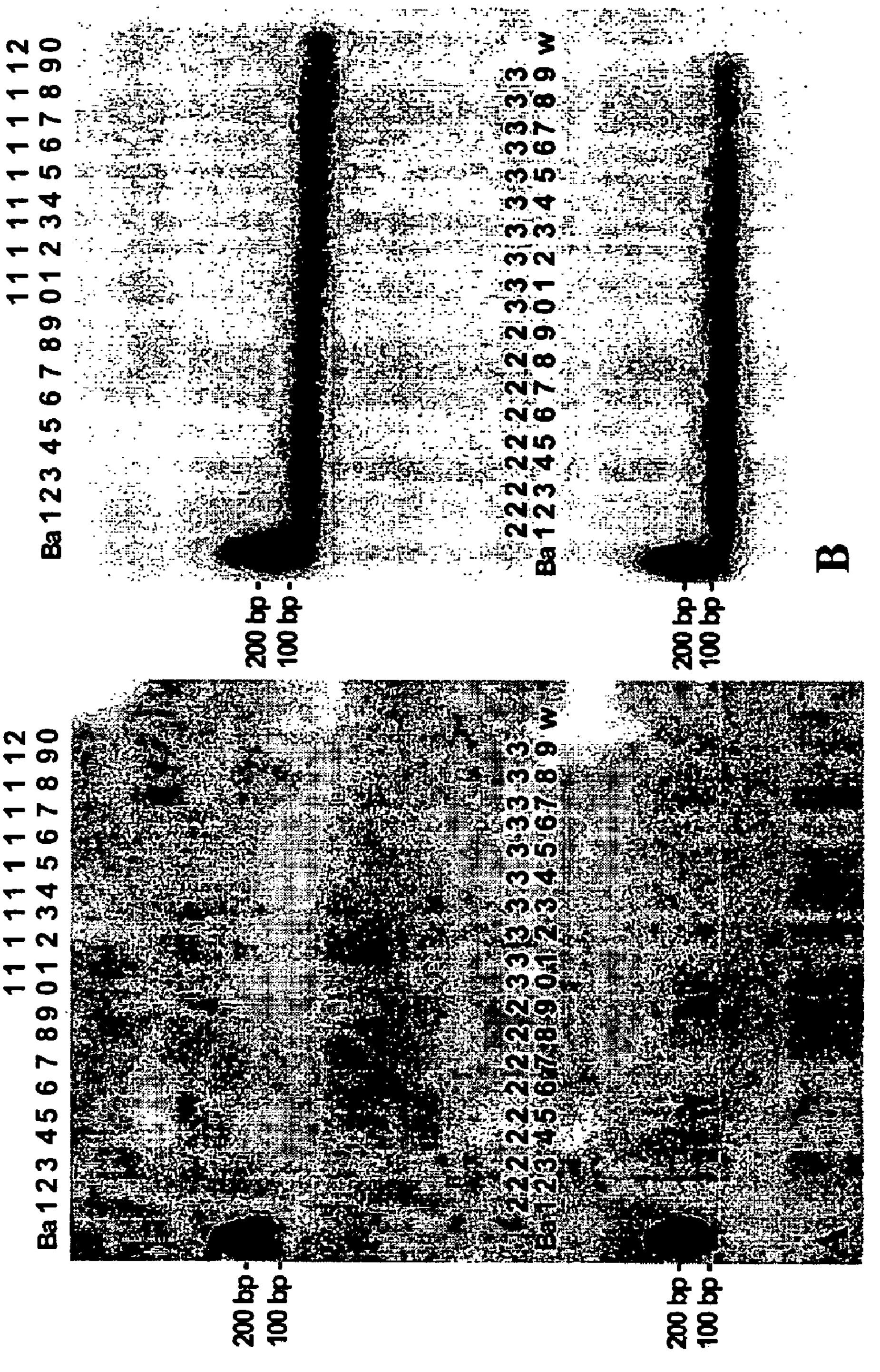
FIG. 3 shows a gel blot showing Southern hybridization analysis of PCR products from 40 *B. cereus* group sspE genotypes using primers sspE-F1/R1.

FIG. 3 shows Southern hybridization analysis of PCR products from 40 *B. cereus* group sspE genotypes using primers sspE-F 1/R1. An sspE gene probe was prepared by DIG PCR labeling method of a 105-bp *B. anthracis* UM23C-1 amplicon. The *B. anthracis* (188-pair amplicon) was detected exclusively (A). The labeled 105-bp probe was removed. The blot was then reprobed with a 71-bp labeled amplicon prepared from *B. cereus* ATCC 14579T genomic DNA. sspE amplicons from *B. cereus*, as well as a 188-bp amplicon of *B. anthracis*, were detected (B). These results indicate that all the PCR products were derived from the sspE gene. Lane numbers represent the same strains as described previously.

Figure 4:
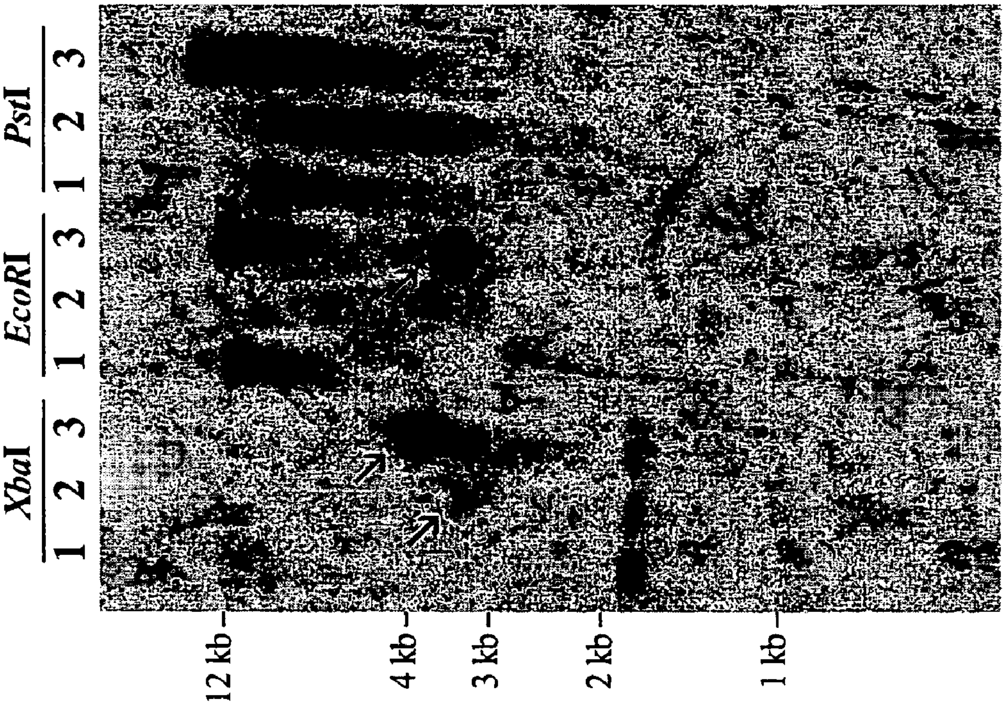
FIG. 4. shows a gel blot of an allele of the sspE gene.

FIG. 4. shows another allele of the sspE gene, discovered by Southern hybridization analysis of genomic DNA from *B. cereus* ATCC 14579T (lane 1), *B. thuringiensis* BGSC 4BG1

(lane 2) and BGSC 4N1 (lane 3) by digestion with XbaI, EcoRI and PstI. After agarose gel electrophoresis, DNA was transferred onto a nylon filter and probed with a DIG-labeled probe to the sspE gene. Arrows indicate the putative second allele of sspE gene.

Figure 5:
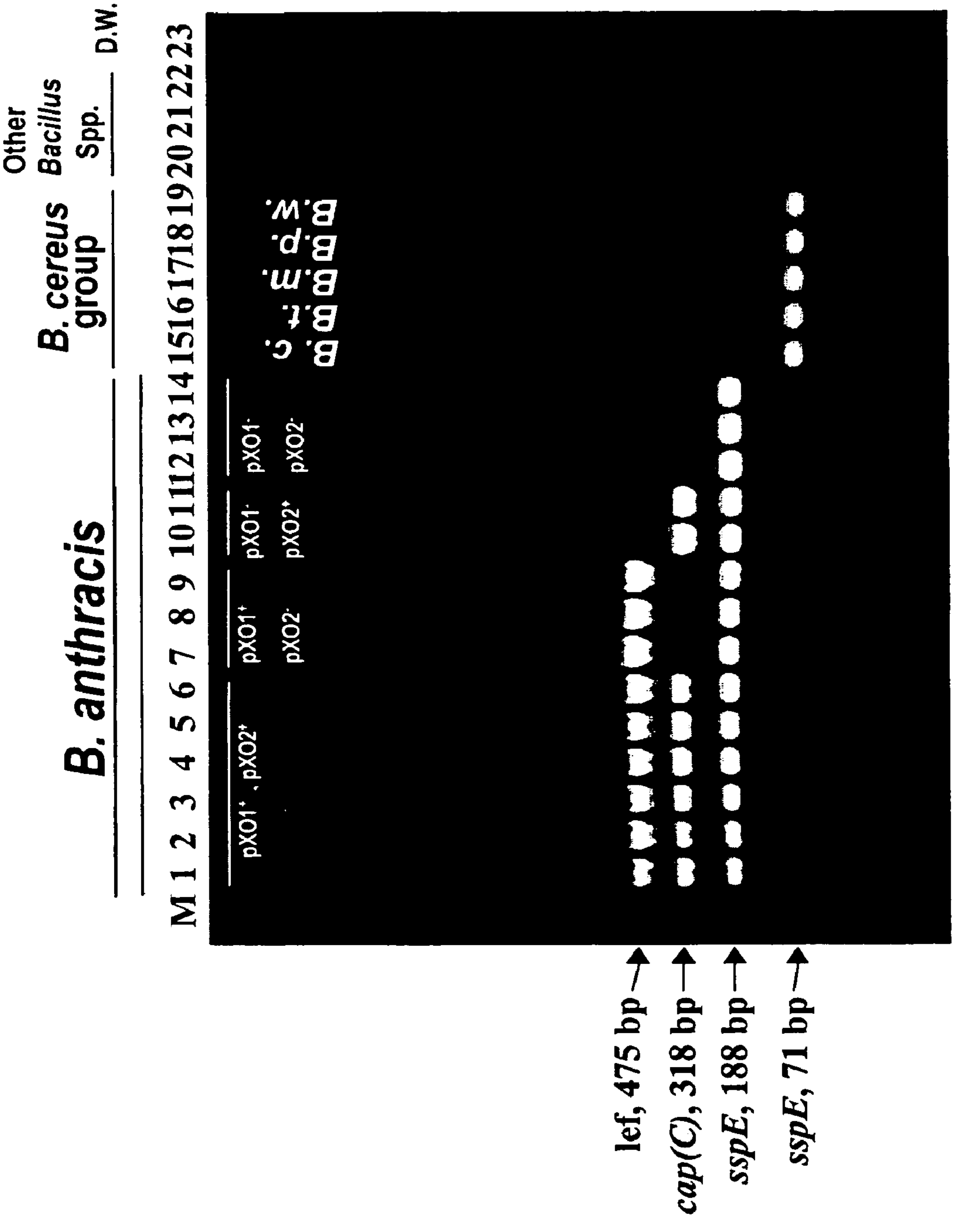
FIG. 5 shows a gel of PCR products that discriminate between various *Bacillus* species and strains.

FIG. 5 shows PCR products that discriminate between *B. anthracis* strains that are fully virulent (lanes 1~6), attenuated containing plasmid pXO1 (lanes 7~9), attenuated containing plasmid pXO2 (lane 10 and 11) or a virulent (lanes 12~14), five different species of the *B. cereus* group (15~19) and non-*Bacillus* spp. (20~22) by a multiplex PCR assay targeting virulent genes on each plasmid (lef for pXO1 plasmid; cap(C) for pXO2) and sspE. Lanes: M, 100-bp DNA size ladder; 1, *B. anthracis* ATCC 14578T; 2, *B. anthracis* CAU 1; 3, *B. anthracis* CAU 2; 4, *B. anthracis* CAU 3; 5, *B. anthracis* CN 1; 6, *B. anthracis* CN 2; 7, *B. anthracis* ATCC 14185; 8, *B. anthracis* ATCC 14186; 9, *B. anthracis* Sterne 34-F2; 10, *B. anthracis* ATCC 4229; 11, *B. anthracis* BC; 12, *B. anthracis* UM23C1-1; 13, *B. anthracis* UM44-1C9; 14, *B. anthracis* Pasteur #2; 15, *B. cereus* ATCC 14579T; 16, *B. thuringiensis* DSM 2046T; 17, *B. mycoides* ATCC 6462T; 18, *B. weihenstephanensis* DSM 11821T; 19, *B. pseudomycoides* DSM 12442T; 20, *B. megaterium* ATCC 14581T; 21, *B. subtilis* ATCC 6051T; 22, *B. licheniformis* ATCC 14580T; 23, negative control (no template DNA).

Further PCR reactions were performed to compare the products obtained using the sspE primers described above, to products obtained using primers for other *Bacillus* loci. These results are displayed in the table shown by Table 3, inserted before the claims, in which the following explains the indicia used in the table: [a]Classified according to proteotypes (P) and genotypes (G) of the sspE gene (2); [b]Plasmids were detected by PCR (6). +, detected; –. not detected; [c]Determined by PCR (4). +, detected; –. not detected; +, false positive reaction; [d]Determined by PCR using primers BA1 and BA2r (7). +, detected; –. not detected; +, false positive reaction; [e]Determined by PCR (5) with some modifications as described in the text, all positive strains were also confirmed by sequencing. +, detected; –. not detected; +, false positive reaction; [f]Haplotype was determined by AluI restriction digestion of the PCR product (1), new types were found (L, M and N). One *B. thuringiensis* strain (BGSC 4CC1) was also determined as the same haplotype (K) as *B. anthracis*, which was also confirmed by sequencing the PCR product; [g]determined by PCR and sequencing (3). Bold face, the length of amplicon which belongs to the category of *B. anthracis* VNTR products; [h]Determined by PCR in this study. +, detected; – no PCR product; –/+, 339-bp amplicon was produced, which is also derived from the sspE gene.

TABLE 3

| No. of | sspE Class[a] | | | | | | | | | | SG-749[g] | |
|---|---|---|---|---|---|---|---|---|---|---|---|---|
| isolate | P | G | Species | Strain | pX01[b] | pX02[b] | Ba813[c] | gyrB[d] | rpoB[e] | cerA[f] | PCR | haplotype |
| 1 | | | *B. anthracis* | ATCC 14578[T] | + | + | + | + | + | + | + | K |
| 2 | | | *B. anthracis* | CAU-1 | + | + | + | + | + | + | + | K |
| 3 | | | *B. anthracis* | CAU-2 | + | + | + | + | + | + | + | K |
| 4 | | | *B. anthracis* | CAU-3 | + | + | + | + | + | + | + | K |
| 5 | | | *B. anthracis* | CN 1 | + | + | + | + | + | + | + | K |
| 6 | | | *B. anthracis* | CN 2 | + | + | + | + | + | + | + | K |
| 7 | | | *B. anthracis* | ATCC 14185 | + | – | + | + | + | + | + | K |
| 8 | | | *B. anthracis* | ATCC 14186 | + | – | + | + | + | + | + | K |
| 9 | | | *B. anthracis* | Sterne 34-F2 | + | – | + | + | + | + | + | K |
| 10 | | | *B. anthracis* | ATCC 4229 | – | + | + | + | + | + | + | K |
| 11 | | | *B. anthracis* | BC | – | + | + | + | + | + | + | K |
| 12 | | | *B. anthracis* | UM 23C1-1 | – | – | + | + | + | + | + | K |
| 13 | | | *B. anthracis* | UM 44-1C9 | – | – | + | + | + | + | + | K |
| 14 | | | *B. anthracis* | Pasieur #2 | – | – | + | + | + | + | + | K |
| 15 | B | 2 | *B. thuringiensis* | BGSC 4BD1 | – | – | + | – | + | + | + | G |
| 16 | C | 8 | *B. thuringiensis* | BGSC 4Y1 | – | – | + | – | + | + | + | G |
| 17 | F | 3 | *Bacillus* spp. | 9594/3 | – | – | + | – | + | + | + | G |
| 18 | F | 3 | *B. thuringiensis* | BGSC 4AY1 | – | – | + | + | – | + | + | L |
| 19 | C | 4 | *Bacillus* spp. | S8553/2 | – | – | + | + | – | + | + | M |
| 20 | C | 4 | *B. cereus* | BGSC 6E1 | – | – | + | + | – | + | + | M |
| 21 | C | 4 | *B. cereus* | BGSC 6E2 | – | – | + | + | – | + | + | M |
| 22 | C | 4 | *Bacillus* spp. | DM 55 | – | – | + | + | – | + | + | M |
| 23 | C | 4 | *Bacillus* spp. | IB | – | – | + | + | – | + | + | M |
| 24 | C | 4 | *Bacillus* spp. | III | – | – | + | + | – | + | + | M |
| 25 | C | 4 | *Bacillus* spp. | III BL | – | – | + | + | – | + | + | M |
| 26 | C | 4 | *Bacillus* spp. | III BS | – | – | + | + | – | + | + | M |
| 27 | C | 4 | *Bacillus* spp. | IV | – | – | + | + | – | + | + | M |
| 28 | C | 4 | *Bacillus* spp. | 003 | – | – | + | + | – | + | + | M |
| 29 | G | | *B. thuringiensis* | BGSC 4AJI | – | – | + | + | – | + | + | E |
| 30 | F | 3 | *Bacillus* spp. | PT030101-01 | – | – | + | + | – | + | + | M |
| 31 | F | 3 | *B. thuringiensis* | BGSC 4CC1 | – | – | + | – | – | + | + | K |
| 32 | F | 3 | *B. thuringiensis* | BGSC 4AB1 | – | – | + | – | – | + | + | E |
| 33 | F | 3 | *B. thuringiensis* | BGSC 4BA1 | – | – | + | – | – | + | + | E |
| 34 | F | 3 | *Bacillus* spp. | 9727 | – | – | + | – | – | + | + | E |
| 35 | F | 3 | *B. thuringiensis* | BGSC 4AS1 | – | – | + | – | – | + | + | N |
| 36 | F | 3 | *B. thuringiensis* | BGSC 4CB1 | – | – | + | – | – | + | + | I |
| 37 | F | 3 | *B. thuringiensis* | BGSC 4BY1 | – | – | + | – | – | + | + | I |
| 38 | C | 9 | *Bacillus* spp. | PT030101-02 | – | – | + | – | – | + | + | I |
| 39 | C | 5 | *B. thuringiensis* | BGSC 4CD1 | – | – | + | – | – | + | + | G |
| 40 | F | 1 | *B. thuringiensis* | BGSC 4BN1 | – | – | + | – | – | + | + | G |
| 41 | H | 1 | *B. cereus* | BGSC 6A7 | – | – | + | – | – | + | + | G |
| 42 | H | 1 | *B. cereus* | BGSC 6A8 | – | – | + | – | – | + | + | G |
| 43 | H | 1 | *Bacillus* spp. | 2A6 | – | – | + | – | – | + | + | G |

TABLE 3-continued

| | | | | | | | | | | | | |
|---|---|---|---|---|---|---|---|---|---|---|---|---|
| 44 | H | 1 | *Bacillus* spp. | 2C1 | − | − | + | − | − | + | + | G |
| 45 | H | 1 | *Bacillus* spp. | 3466-8.1 | − | − | + | − | − | + | + | G |
| 46 | H | 1 | *Bacillus* spp. | PEYR 8 | − | − | + | − | − | + | + | G |
| 47 | H | 1 | *Bacillus* spp. | PEYR 9 | − | − | + | − | − | + | + | G |
| 48 | H | 2 | *Bacillus* spp. | PEYR 6 | − | − | + | − | − | + | + | G |
| 49 | H | 2 | *B. thuringiensis* | BGSC 4AN1 | − | − | + | − | − | + | + | G |
| 50 | H | 2 | *B. thuringiensis* | BGSC 4AF1 | − | − | + | − | − | + | + | G |
| 51 | H | 2 | *B. thuringiensis* | BGSC 4AQ1 | − | − | + | − | − | + | + | G |
| 52 | H | 2 | *B. thuringiensis* | BGSC 4U1 | − | − | + | − | − | + | + | G |
| 53 | L | | *B. thuringiensis* | BGSC 4AX1 | − | − | + | − | − | + | + | H |
| 54 | L | | *B. thuringiensis* | BGSC 4AW1 | − | − | + | − | − | + | + | H |
| 55 | I | | *Bacillus* spp. | 12 | − | − | + | − | − | + | + | H |

| No. of | Multiple-Locus VNTR[h] | | | | | | sspE[i] | | | | |
|---|---|---|---|---|---|---|---|---|---|---|---|
| | | | | | | | F1/R1 | | F2/R2 | F3/R3 | |
| isolate | vrrA | $vrrB_1$ | $vrrB_2$ | $vrrC_1$ | $vrrC_2$ | CG3 | 71 bp | 188 bp | 105 bp | 117 bp | 234 bp |
| 1 | 290 | 229 | 153 | 535 | 604 | 158 | + | + | + | + | + |
| 2 | 314 | 229 | 162 | 616 | 532 | 158 | + | + | + | + | + |
| 3 | 314 | 229 | 162 | 688 | 532 | 158 | + | + | + | + | + |
| 4 | 314 | 229 | 162 | 616 | 532 | 158 | + | + | + | + | + |
| 5 | 302 | 256 | 171 | 580 | 532 | 158 | + | + | + | + | + |
| 6 | 302 | 256 | 171 | 580 | 532 | 158 | + | + | + | + | + |
| 7 | 314 | 229 | 162 | 616 | 532 | 158 | + | + | + | + | + |
| 8 | 314 | 229 | 162 | 616 | 532 | 158 | + | + | + | + | + |
| 9 | 314 | 229 | 162 | 580 | 532 | 158 | + | + | + | + | + |
| 10 | 314 | 229 | 162 | 616 | 604 | 158 | + | + | + | + | + |
| 11 | 314 | 229 | 162 | 580 | 532 | 158 | + | + | + | + | + |
| 12 | 314 | 229 | 162 | 580 | 532 | 158 | + | + | + | + | + |
| 13 | 314 | 229 | 162 | 580 | 532 | 158 | + | + | + | + | + |
| 14 | 314 | 229 | 162 | 580 | 532 | 158 | + | + | + | + | + |
| 15 | 290 | — | 171 | 724 | 478 | — | + | − | − | − | + |
| 16 | 284 | — | 243 | — | 622 | — | + | − | − | − | + |
| 17 | 308 | — | 198 | — | 550 | — | + | − | − | − | + |
| 18 | 296 | 283 | 258 | 571 | 586 | 158 | + | − | − | − | + |
| 19 | 284 | 256 | 243 | 535 | — | 158 | + | − | − | − | + |
| 20 | 284 | — | — | 499 | 478 | 158 | + | − | − | − | + |
| 21 | 284 | — | — | 499 | 478 | 158 | + | − | − | − | + |
| 22 | 284 | — | — | 391 | 586 | 158 | + | − | − | − | + |
| 23 | 284 | — | — | 391 | 658 | 158 | + | − | − | − | + |
| 24 | 284 | — | — | 391 | 658 | 158 | + | − | − | − | + |
| 25 | 284 | — | — | 391 | 640 | 158 | + | − | − | − | + |
| 26 | 284 | — | — | 391 | 658 | 158 | + | − | − | − | + |
| 27 | 284 | — | — | 391 | 658 | 158 | + | − | − | − | + |
| 28 | 284 | — | — | 391 | 658 | 158 | + | − | − | − | + |
| 29 | 308 | 175 | 252 | 571 | 730 | 158 | + | − | − | − | + |
| 30 | 290 | 328 | 234 | 319 | 658 | 158 | + | − | − | − | + |
| 31 | 308 | 292 | 189 | 616 | 712 | 158 | + | − | − | − | + |
| 32 | 296 | 295 | 198 | 529 | 748 | 158 | + | − | − | − | + |
| 33 | 296 | 295 | 198 | 529 | 748 | 158 | + | − | − | − | + |
| 34 | 272 | 283 | 189 | 571 | 712 | 158 | + | − | − | − | + |
| 35 | 296 | 256 | 171 | 499 | 694 | 158 | + | − | − | − | + |
| 36 | 296 | 292 | 198 | 499 | 640 | 158 | + | − | − | − | + |
| 37 | 296 | 292 | 198 | 499 | 640 | 158 | + | − | − | − | + |
| 38 | 296 | 292 | 216 | 697 | 406 | 158 | + | − | − | − | + |
| 39 | 320 | — | 243 | 823 | 478 | — | + | − | − | − | + |
| 40 | 314 | — | — | — | — | — | + | − | − | − | + |
| 41 | 314 | — | — | — | — | — | + | − | − | − | + |
| 42 | 314 | — | — | — | — | — | + | − | − | − | + |
| 43 | 338 | — | — | — | — | — | + | − | − | − | + |
| 44 | 338 | — | — | — | — | — | + | − | − | − | + |
| 45 | 326 | — | — | — | — | — | + | − | − | − | + |
| 46 | 326 | — | — | — | — | — | + | − | − | − | + |
| 47 | 326 | — | — | — | — | — | + | − | − | − | + |
| 48 | 326 | — | — | — | — | — | + | − | − | − | + |
| 49 | 308 | — | — | — | — | — | + | − | − | − | + |
| 50 | 296 | — | — | — | — | — | + | − | − | − | + |
| 51 | 296 | — | — | — | — | — | + | − | − | − | + |
| 52 | 284 | — | — | — | — | — | + | − | − | − | + |
| 53 | 278 | — | — | 718 | 478 | — | + | − | − | − | −/+ |
| 54 | 278 | — | — | 718 | 478 | — | + | − | − | − | −/+ |
| 55 | 284 | — | — | 529 | 586 | — | + | − | − | − | + |

A large number of strains of various *Bacillus* species were tested with various PCR primer pairs to further determine their specificity. These results are shown in Table 4, where "–" is no PCR product and "+" indicates a PCR product.

TABLE 4

Further specificity analysis with sspE and other chromosomal assays.

| Total No Strains | Species | Ba813 | gyrB | rpoB | SG747 | sspE F1/R1 71 bp | sspE F1/R1 188 bp | sspE F2/R2 105 bp | sspE F3/R3 117 bp | sspE F3/R3 234 bp |
|---|---|---|---|---|---|---|---|---|---|---|
| 9 | *B. cereus* | – | – | – | + | + | – | – | – | + |
| 14 | *B. thuringiensis* | – | – | – | 111+ 3– | + | – | – | – | + |
| 7 | *B. mycoides* | – | – | – | + | + | – | – | – | + |
| 1 | *B. pseudomycoides* | – | – | – | + | + | – | – | – | + |
| 1 | *B. weihenstephanensis* | – | – | – | + | + | – | – | – | + |
| 3 | *Bacillus* spp. | – | – | – | + | + | – | – | – | + |
| 64 | Other *Bacillus* spp | – | – | – | – | – | – | – | – | – |
| 17 | Non-bacillus bacteria | – | – | – | – | – | – | – | – | – |

A summary of the results of the above described PCR assays is found in Tables 5 and 6.

TABLE 5

Summary comparison of specificity and sensitivity of PCR assays for detection of *B anthracis*

| | Ba813 PCR | gyrB PCR | rpoB PCR | SG-749 Haplotype | sspE F1/R1 | sspE F2/R2 | SspE F3/R3 |
|---|---|---|---|---|---|---|---|
| No. false positives | 42 | 13 | 3 | 1 | 0 | 0 | 0 |
| No. non-*B. anthracis* tested | 258 | 258 | 258 | 42 | 258 | 258 | 258 |
| Specificity | 83.7% | 95% | 98.8% | 97.6% | 100% | 100% | 100% |
| No. false negative | 0 | 0 | 0 | 0 | 0 | 0 | 0 |
| No. *B. anthracis* tested | 14 | 14 | 14 | 14 | 14 | 14 | 14 |
| Sensitivity | 100% | 100% | 100% | 100% | 100% | 100% | 100% |

TABLE 6

Summary comparison of specificity and sensitivity of PCR assays for detection of the *B. cereus* group.

| | cerA-PCR | SG-749 PCR | sspE F1/R1 | sspE F3/R3 |
|---|---|---|---|---|
| No. false positives | 0 | 0 | 0 | 0 |
| No of non-*B. cereus* group tested | 81 | 81 | 81 | 81 |
| Specificity | 100% | 100% | 100% | 100% |
| No. of false negatives | 3 | 0 | 0 | 0 |
| No. of *B. cereus* group tested | 191 | 191 | 191 | 191 |
| Sensitivity | 98.4% | 100% | 100% | 100% |

In summary:

1) PCR with primers sspE-F1/R1 (FIG. 2A). *B. anthracis* produced 188- and 71-bp amplicons (the 188-bp amplicon is *B. anthracis* specific). The *B. cereus* group produced a 71-bp amplicon only. Other *Bacillus* and non-*Bacillus* bacteria: no amplicon. Specificity 100% (determined from 258 strains). Sensitivity 100% (determined from 14 strains).

2) PCR with primers sspE-F2/R2 (FIG. 2B). Only *B. anthracis* produced a 105-bp amplicon. Other bacteria produced no amplicon. Specificity 100% (determined from 258 strains). Sensitivity 100% (determined from 14 strains)

3) PCR with primers sspE-F3/R3 (FIG. 2C). *B. anthracis* produced 117- and 234-bp amplicons (the 117-bp amplicon is *B. anthracis* specific). The *B. cereus* group produced a 234-bp amplicon only, except 2 strains produced an additional longer product of 339 bp. 1 strain produced only the 339-bp amplicon, which is an additional sspE allele (FIG. 4.). Other *Bacillus* and non-*Bacillus* bacteria produced no expected amplicon. Specificity 100% (determined from 258 strains). Sensitivity 100% (determined from 14 strains)

Other assays showed varying degrees of false positive reactions but 100% sensitivity for the detection of *B. anthracis* (Table 3, 4).

Both PCR assays with sspE-F1/R1 and sspE-F3/R1 detected the *B. cereus* group with absolute specificity in accordance with SG-749 PCR but cerA PCR produced three false negative reactions.

A multiplex PCR assay was developed that discriminates between of all *B. anthracis* plasmid virulence types, the *B. cereus* group and other *Bacillus* species or non-*Bacillus* bacteria (FIG. 5).

Example 2

Materials and Methods

Bacterial strains and DNA isolation: A total of 38 bacterial strains used in this second study are shown in Table 7. The strains, except for *B. anthracis*, were acquired from the American Type Culture Collection (Manassas, Va., USA),

*Bacillus* Genetic Stock Center (Department of Biochemistry, The Ohio State University, Columbus, Ohio, USA) and Deutsche Sammlung von Mikroorganismen und Zellkulturen (Braunschweig, Germany). *B. anthracis* genomic DNA preparations were a gift from Chung-Ang University Medical College. Genomic DNA from other strains was isolated using the Easy-DNA kit (Invitrogen Corp., CA, USA) according to the manufacturer's protocol. DNA concentrations were determined spectrophotometrically and diluted to 10 ng $\mu l^{-1}$ in sterile distilled water. Both the quality and quantity of the DNA were evaluated following electrophoresis in a 0.7% agarose gel containing ethidium bromide (0.5 $\mu g\ ml^{-1}$).

Primers: The chromosomal and plasmid primers used for PCR detection of *B. anthracis* are shown in Table 8. The sspE-1 primer pair targets the sspE chromosomal gene producing 188- or 71-bp amplicons. The cap-29 primer pair targets the cap(C) gene of the pXO2 plasmid and produces a 318-bp amplicon. The lef-4 primer pair targets the lef gene of the pXO1 plasmid and produces a 475-bp amplicon. To evaluate the applicability of these primers for multiplex detection of each amplicon by melting curve analysis, the melting temperature ($T_m$) of each amplicon was calculated using Oligo® V6.5 software (Molecular Biology Insights Inc., Cascade, Colo., USA).

TABLE 7

Bacterial strains used in this study and their DNA-based assay response.

| | | | Plasmid[b] | | PCR for: | | | | SG-749 [g] | | sspE PCR[h] | |
|---|---|---|---|---|---|---|---|---|---|---|---|---|
| Species | Strain ID | Source[a] | pXO1 | pXO2 | Ba813[c] | gyrB[d] | rpoB[e] | gyrA[f] | PCR | Haplotype | 71 bp | 188 bp |
| *B. anthracis* | 14578$^{T}$ | ATCC | + | + | + | + | + | + | + | K | + | + |
| *B. anthracis* | CAU-1 | Korea | + | + | + | + | + | + | + | K | + | + |
| *B. anthracis* | CAU-2 | Korea | + | + | + | + | + | + | + | K | + | + |
| *B. anthracis* | CAU-3 | Korea | + | + | + | + | + | + | + | K | + | + |
| *B. anthracis* | CN1 | Korea | + | + | + | + | + | + | + | K | + | + |
| *B. anthracis* | CN2 | Korea | + | + | + | + | + | + | + | K | + | + |
| *B. anthracis* | 14185 | ATCC | + | − | + | + | + | + | + | K | + | + |
| *B. anthracis* | 14186 | ATCC | + | − | + | + | + | + | + | K | + | + |
| *B. anthracis* | Sterne 34-F2 | | + | − | + | + | + | + | + | K | + | + |
| *B. anthracis* | BC | China | − | + | + | + | + | + | + | K | + | + |
| *B. anthracis* | Pasteur #2 | | − | − | + | + | + | + | + | K | + | + |
| *B. thuringiensis* | 4BG1 | BGSC | − | − | + | − | + | − | + | G | + | − |
| *B. thuringiensis* | 4Y1 | BGSC | − | − | + | − | + | − | + | G | + | − |
| *Bacillus* spp. | 9594/3 | Patra G. | − | − | + | − | + | − | + | G | + | − |
| *B. thuringiensis* | 4AY1 | BGSC | − | − | + | + | − | + | + | L | + | − |
| *B. thuringiensis* | 4AJ1 | BGSC | − | − | + | + | − | + | + | E | + | − |
| *B. cereus* | 6E1 | BGSC | − | − | + | + | − | − | + | M | + | − |
| *Bacillus* spp. | IB | Rogers J. E. | − | − | + | + | − | − | + | M | + | − |
| *Bacillus* spp. | III | Rogers J. E. | − | − | + | + | − | − | + | M | + | − |
| *Bacillus* spp. | 003 | Rogers J. E. | − | − | + | + | − | − | + | M | + | − |
| *B. thuringiensis* | 4CC1 | BGSC | − | − | + | − | − | − | + | **K** | + | − |
| *B. cereus* | 6A7 | BGSC | − | − | + | − | − | − | + | G | + | − |
| *B. thuringiensis* | 4AB1 | BGSC | − | − | + | − | − | − | + | E | + | − |
| *Bacillus* spp. | 9727 | Hernandez E. | − | − | + | − | − | − | + | E | + | − |
| *B. cereus* | 14579$^{T}$ | ATCC | − | − | − | − | − | − | + | A | + | − |
| *B. thuringiensis* | 2046$^{T}$ | DSM | − | − | − | − | − | − | + | A | + | − |
| *B. pseudomycoides* | 12442$^{T}$ | DSM | − | − | − | − | − | − | + | J | + | − |
| *B. weihenstephanensis* | 11821$^{T}$ | DSM | − | − | − | − | − | − | + | G | + | − |
| *B. mycoides* | 6462$^{T}$ | ATCC | − | − | − | − | − | − | + | G | + | − |
| *B. subtilis* | 6051$^{T}$ | ATCC | − | − | − | − | − | − | − | NA[i] | − | − |
| *B. megaterium* | 14581$^{T}$ | ATCC | − | − | − | − | − | − | − | NA | − | − |
| *B. licheniformis* | 14580$^{T}$ | ATCC | − | − | − | − | − | − | − | NA | − | − |
| *B. circulans* | 4513$^{T}$ | ATCC | − | − | − | − | − | − | − | NA | − | − |
| *Escherichia coli* | 4157 | ATCC | − | − | − | − | − | − | − | NA | − | − |
| *Enterbacter aerogenes* | 13048$^{T}$ | ATCC | − | − | − | − | − | − | − | NA | − | − |
| *Salmonella choleraesuis* | 13076$^{T}$ | ATCC | − | − | − | − | − | − | − | NA | − | − |
| *Pseudomonas aeruginosa* | 10145$^{T}$ | ATCC | − | − | − | − | − | − | − | NA | − | − |
| *Clostridium sporogenes* | 3584$^{T}$ | ATCC | − | − | − | − | − | − | − | NA | − | − |

[a]ATCC, American Type Culture Collection, Manassas, VA, USA; BGSC, Bacillus Genetic Stock Center, Department of Biochemistry, The Ohio State University, Columbus, OH, USA; DSM, Deutsche Sammlung von Mikroorganismen und Zellkulturen, Braunschweig, Germany

[b]Plasmids were detected by PCR (51). +, detected; −. not detected

[c]Determined by PCR (25). +, detected; −. not detected; +, false positive reaction

[d]Determined by PCR using primers BA1 and BA2r (30). +, detected; −. not detected; +, false positive reaction.

[e]Determined by PCR and sequencing (32). +, detected; −. not detected; +, false positive reaction.

[f]Determined by PCR and sequencing (33). +, detected; −. not detected; +, false positive reaction.

[g]Determined by PCR and its haplotype was determined by AluI restriction digestion of the PCR product (31). +, detected; −. not detected; K, false positive reaction.

[h]Determined by PCR (manuscript in preparation). +, detected; −. not detected.

[i]Not applicable

TABLE 8

Nucleotide sequences of multiplex real-time PCR primers. From top to bottom, the SEQ ID NOS of these primers are: SEQ ID NO: 1, SEQ ID NO: 2, SEQ ID NO: 7, SEQ ID NO: 8, SEQ ID NO: 9 and SEQ ID NO: 10.

| Loci | Primers | Sequence (5'→3') | Product (bp)[a] | $T_m$(° C.)[b] |
|---|---|---|---|---|
| sspE | sspE1-F | GAGAAAGATGAGTAAAAAACAACAA | **188**, 71 | 60.9 |
| (Chromosome) | sspE1-R | CATTTGTGCTTTGAATGCTAG | | 59.5 |
| lef | lef4-F | TGAACCCGTACTTGTAATCCAATC | **475** | 67.6 |
| (pXO1) | lef4-R | ATCGCTCCAGTGTTGATAGTGCT | | 68.0 |
| cap(C) | cap29-F | GTTGTACCTGGTTATTTAGCACTC | **318** | 62.7 |
| (pXO2) | cap29-R | ACCACTTAACAAAATTGTAGTTCC | | 62.3 |

[a]Boldface, *B. anthracis* specific amplicons
[b]Calculated by the nearest - neighbor method; $T_m$, melting temperature Measurement of Amplicon $T_m$. Simplex real-time PCR triplicate samples was utilized to measure the average $T_m$ of amplicons from the sspE, cap(C) and lef genes. The reaction mixture (20 μl) contained 2 μl of 10× LightCycler FastStart DNA Master SYBR Green I (10 mM $MgCl_2$ is contained), 0.5 μM of each primer (Table 8), 10 ng of template DNA, and an additional 2 mM of $MgCl_2$ to make a final concentration of 3 mM $MgCl_2$. Cycling conditions were preincubation for 10 min at 95° C., 40 cycles of 10 s at 95° C., 2 s at 58° C. and 25 s at 72° C. A melting curve was generated by measuring the fluorescent signal while raising the temperature slowly as follows: 0 s at 95° C., 30 s at 65° C. and temperature increase from 65° C. to 95° C. with 0.1° C. $s^{-1}$ of temperature transition rate. The $T_m$ was measured using the LightCycler software V 3.5.

Multiplex real-time PCR.: To detect the virulence plasmids and chromosome of *B. anthracis* simultaneously, optimal multiplex real-time PCR conditions were determined. PCR conditions were the same as those described above for the simplex PCR except that 0.5 μM sspE-1 primers, 0.25 μM lef-4 primers, and 0.3 μM cap-29 primers were added to the reaction mixture, extension temperature was 65° C., and the temperature transition rate for the melting curve analysis was 0.05° C. $s^{-1}$. Multiplex amplification products were also confirmed by electrophoresis using a 2% agarose gel containing 0.5 μg ethidium bromide per ml of gel solution. Detection sensitivity of the multiplex assay was determined by dilution to extinction PCR (50 ng to 500 fg of genomic DNA).

Results

Figure 7:
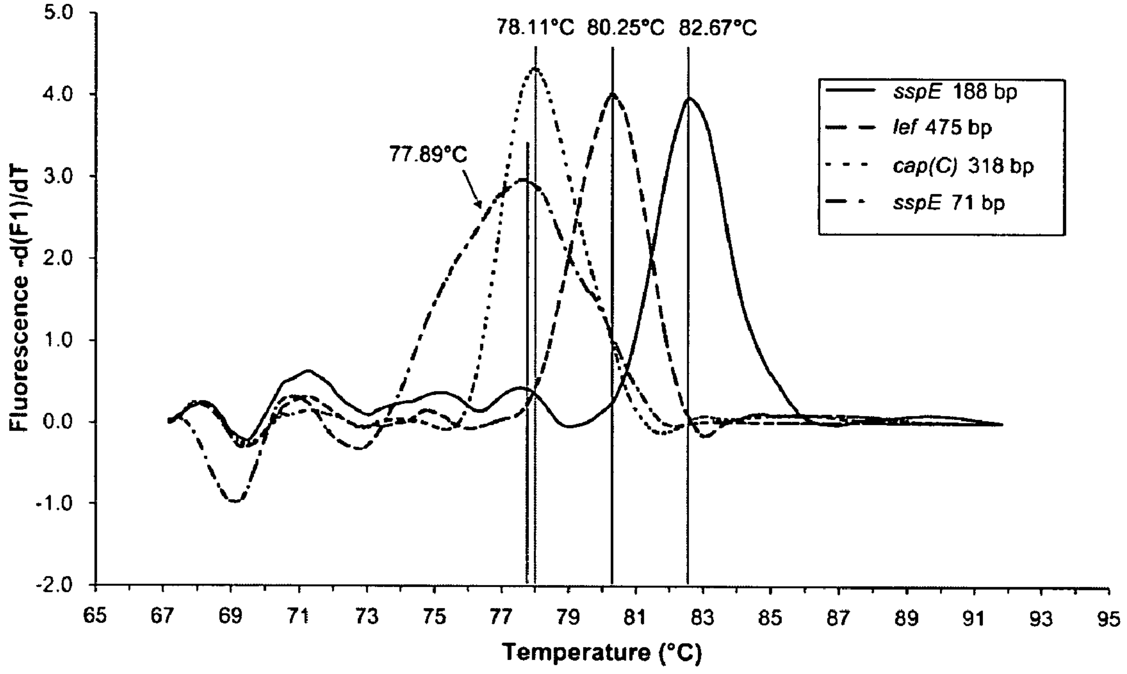
FIG. 7 is a graph showing the results of simplex real-time PCR and melting curve analysis to measure the melting temperatures of three amplicons from the genomic DNA of *B. anthracis* ATCC $14578^T$ and one amplicon from the genomic DNA of *B. cereus* ATCC $14579^T$. The melting temperature was determined using LightCycler software V 3.5. The three amplicons representing the two virulence plasmids and the chromosome of *B. anthracis* generated sharp melting peaks. The *B. cereus* amplicon produced one broad melting peak without the sspE peak representing the chromosome of *B. anthracis*. The y axis is the negative differential of fluoresecence over temperature (−dF/dT).

Calculation and Measurement of PCR Amplicon $T_m$ $T_m$s of all possible amplicons that can be produced from *B. anthracis* DNA using the three primer pairs were preliminarily estimated by calculations with Oligo® V6.5 software and are shown in Table 93. The differences between the software-estimated $T_m$s ranged from 1 to 7.8° C. The amplicons showing the smallest $T_m$ differences (1° C.) were lef and cap(C). The $T_m$ of these two amplicons was measured in triplicate samples by simplex real-time PCR and melting curve analysis (Table 9, FIG. 7). Measured $T_m$s of two sspE-targeting amplicons (188 bp and 71 bp) using the LightCycler software were similar to their estimated $T_m$s by the Oligo® software. The measured $T_m$ of the lef amplicon (80.19±0.07° C.) was ~1° C. less than its estimated $T_m$ (81.3° C.). The measured $T_m$ of cap(C) amplicon (77.96±0.13° C.) was ~2° C. less than its estimated $T_m$ (80.3° C.). Contrary to the software predicted difference (1° C.) between the $T_m$s of lef and cap(C) amplicons, the real-time PCR melting curve analysis demonstrated a larger difference (~2° C.) between these two PCR products. However, the $T_m$ difference between the small sspE (71 bp) and cap(C) amplicons, which was estimated to be ~1.8° C., was measured as 0.42-0.74° C. by real-time PCR.

TABLE 9

Calculated and measured melting temperatures ($T_m$) of amplicons targeting sspE, lef, and cap(C).

| | Product | | | | |
|---|---|---|---|---|---|
| Target | Length (bp) | GC (%) | Calculated $T_m$ (° C.)[a] | Measured $T_m$ (° C.)[b] | Measured $T_m$ ° C.)[c] |
| sspE | 188 | 39.4 | 82.6 | 82.69 ± 0.03 | 83.59 ± 0.40 |
| | 71 | 36.6 | 77.1 | 77.41 ± 0.04 | 76.56 ± 0.96 |
| lef | 475 | 32.2 | 81.3 | 80.19 ± 0.07 | 79.97 ± 0.53 |
| cap(C) | 318 | 31.1 | 80.3 | 77.96 ± 0.13 | 77.86 ± 0.30 |

[a]Obtained by using Oligo V6.5 software
[b]Obtained by simplex real-time PCR and melting curve analysis using LightCycler V3.5 software, mean ± S.D.
[c]Obtained by multiplex real-time PCR and melting curve analysis using LightCycler V3.5 software, mean ± S.D.

Figures 8A, 8B:
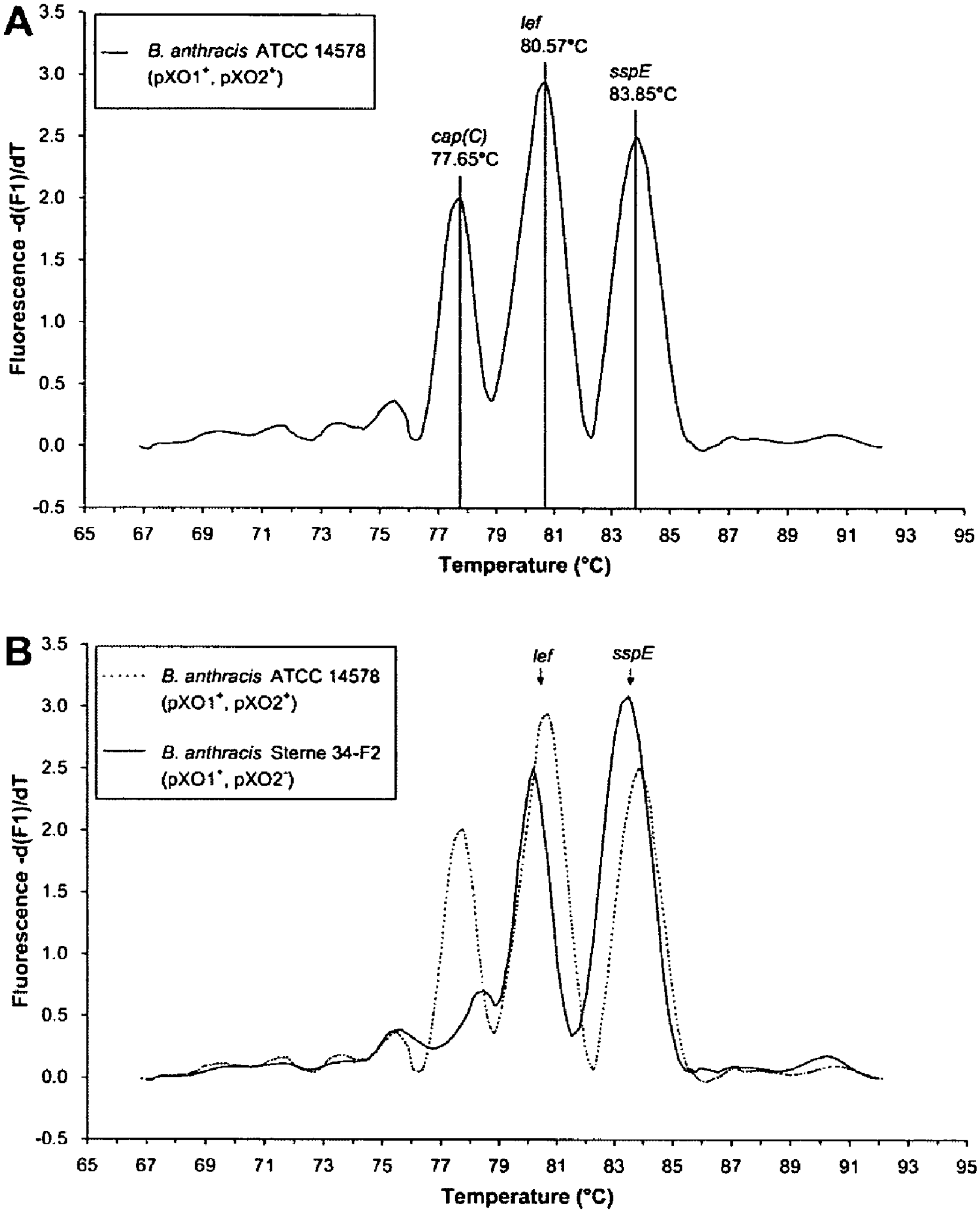
FIGS. 8A-8E are graphs showing the results of multiplex real-time PCR and melting curve analysis performed with three multiple pairs of primers targeting four chromosomal and plasmid genes. The four plasmid genotypes of *B. anthracis*, and the *B. cereus* group chromosome, were differentially detected by amplicon thermal melting analysis. Template DNAs were from: *B. anthracis* ATCC $14578^T$, Panel A; *B. anthracis* Sterne 34-F2, Panel B; *B. anthracis* BC, Panel C; *B. anthracis* Pasteur #2, Panel D; and Panel E; *B. anthracis* ATCC $14578^T$ and *B. cereus* ATCC $14579^T$.
Figures 8C, 8D, 8E:
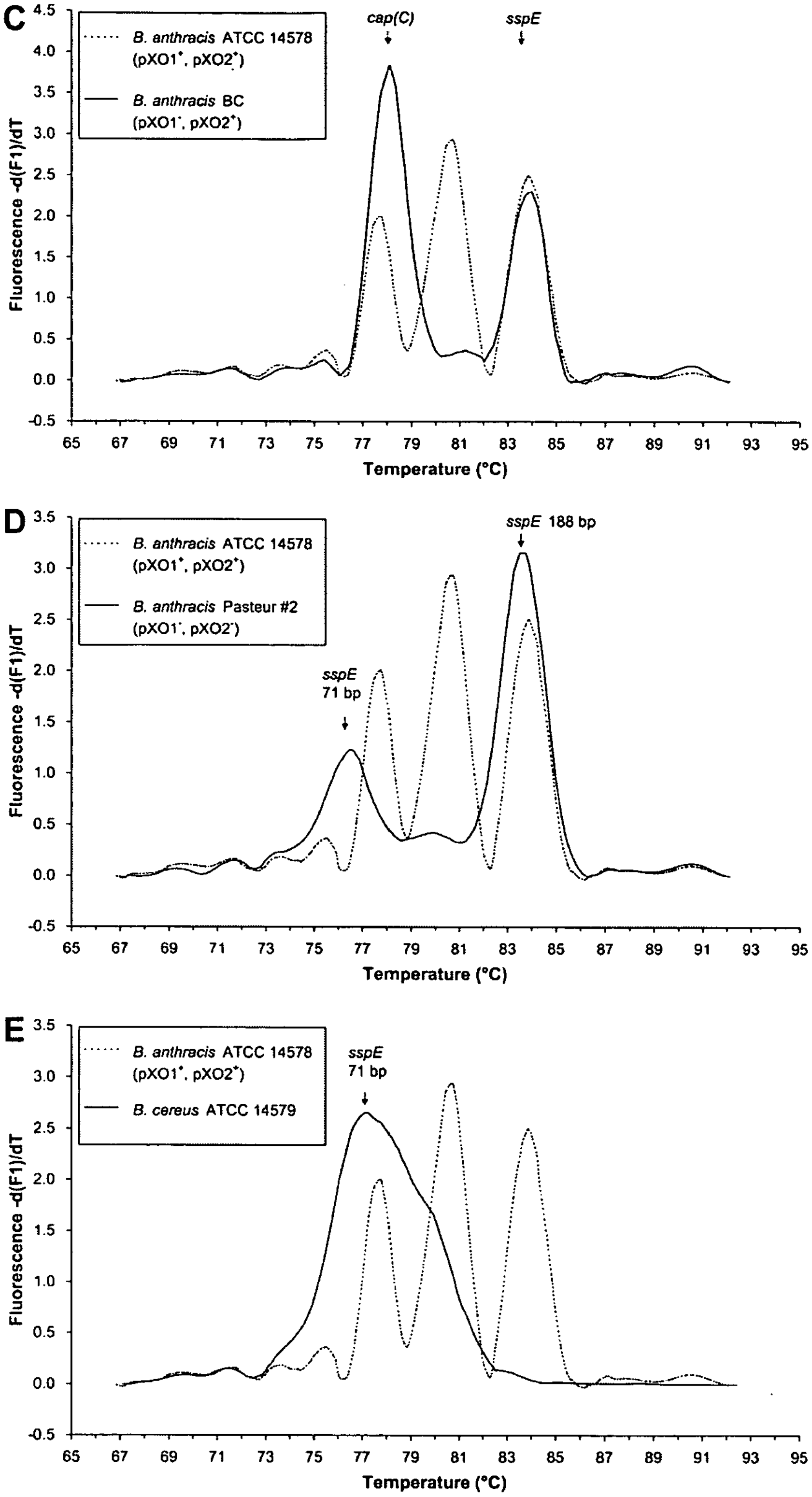

Simultaneous Differential Identification of *B. anthracis* Genotypes and the *B. cereus* Group using Multiplex Real-Time PCR and Melting Curve Analysis Multiplex real-time PCR and melting curve analysis was carried out by including three multiple pairs of primers targeting three genes located on the chromosome and virulence plasmids to determine if melting curve analysis can simultaneously discriminate among all amplicons. With DNA from virulent *B. anthracis* ($pXO1^+$, $pXO2^+$), the melting curve analysis of multiplex real-time PCR detected three amplicons, the sspE gene from the chromosome, the lef gene from the pXO1 plasmid and the cap(C) gene from the pXO2 plasmid (FIG. 8A). The small sspE (71 bp) amplicon was not resolved in these reactions. Compared to the $T_m$s previously measured by melting curve analysis in simplex real-time PCR, the $T_m$ of the large sspE (188 bp) and lef amplicons deviated slightly (+0.9° C. and −0.21° C. respectively) from the $T_m$s measured in simplex real-time PCR. The $T_m$ of the cap(C) amplicon also deviated slightly (−0.1° C.) from the estimated $T_m$. These deviations resulted in improved separation of the melting peaks, allowing improved multiplex amplicon discrimination. Using Stern type *B. anthracis* ($pXO1^+$, $pXO1^-$) template DNA, the melting curve peaks representing the lef and sspE amplicons appeared without the cap(C) peak (FIG. 8B). The small sspE amplicon was not detected. Using *B. anthracis* template DNA derived from a strain carrying only the pXO2 plasmid, melting peaks representing the cap(C) and sspE amplicons were produced without the lef amplicon (FIG. 8C). The small sspE amplicon was not detected. Using *B. anthracis* template DNA derived from a strain carrying no plasmids ($pXO1^-$, $pXO2^-$), in addition to the 188-bp sspE peak at ~83.6° C., there was also a prominent melting peak at ~76.5° C. representing the small amplicon of sspE (71 bp) (FIG. 8D). Using template DNA from *B. cereus* group species, only the melting peak representing the small amplicon of sspE appeared as a broad peak at ~77° C. (FIG. 8E). Thus, all plasmid genotypes of *B. anthracis* and strains from the *B. cereus* group were discriminated simultaneously by multiplex real-time PCR melting curve analysis.

Agarose Gel Analysis of Real-Time PCR Products

Figure 9:
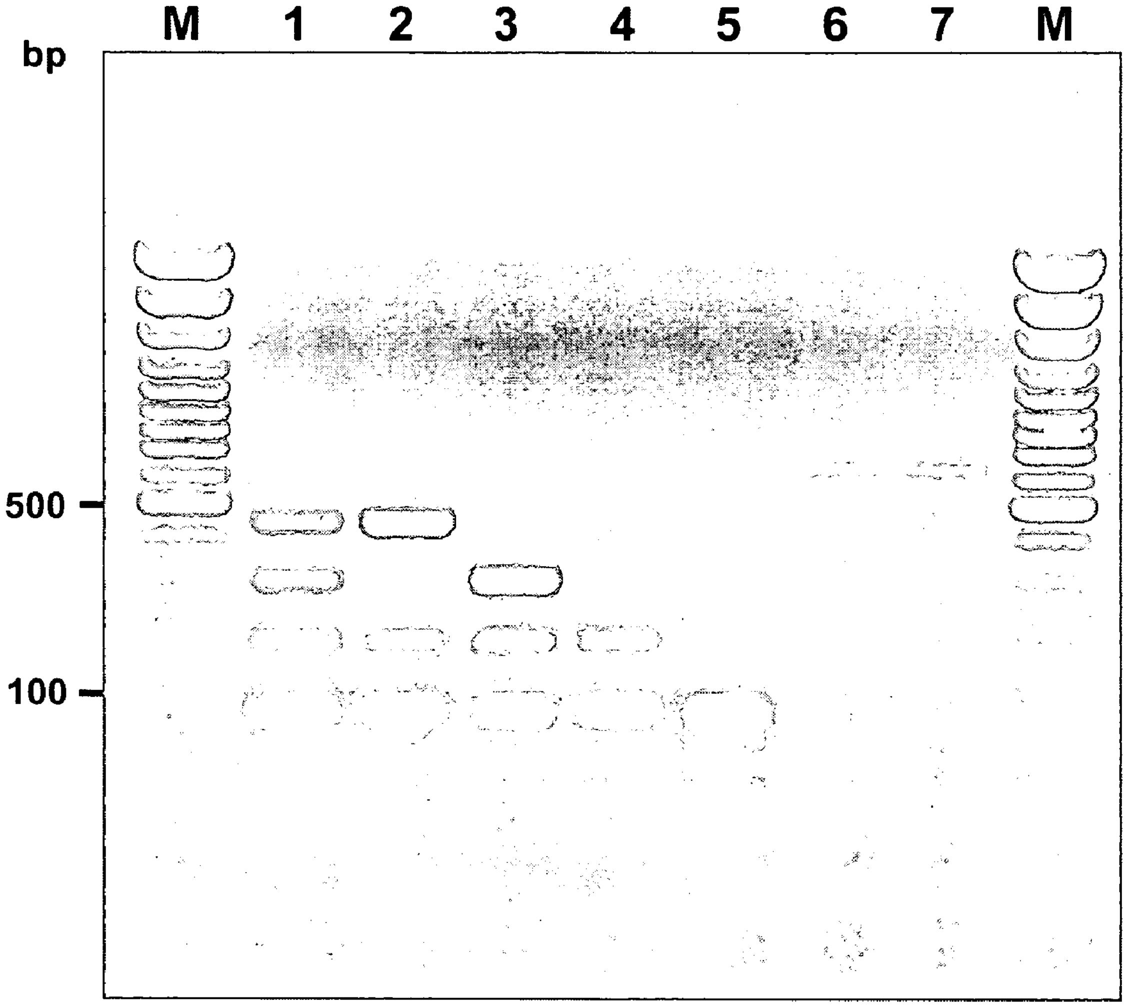
FIG. 9 is an image of a gel showing the results of agarose gel analysis of multiplex real-time PCR products. All target amplicons expected from the plasmids and chromosomes of *B. anthracis* and *B. cereus* strains were confirmed by agarose gel electrophoresis. Lane M, 100 bp DNA ladder; lane 1, *B. anthracis* ATCC $14578^T$; lane 2, *B. anthracis* Sterne 34-F2; lane 3, *B. anthracis* BC; lane 4, *B. anthracis* Pasteur #2; lane 5, *B. cereus* ATCC $14579^T$; lane 6, *B. subtilis* ATCC $6051^T$; and lane 7, negative water control.

Agarose gel analysis of the multiplex real-time PCR reactions confirmed the expected PCR products (FIG. 9). In contrast to the melting curve analysis of the three *B. anthracis* genotypes, which did not reveal the small sspE amplicon, agarose gel analysis did detect this PCR product.

Examination of Assay Specificity and Sensitivity

The *B. anthracis* multiplex real-time PCR assay did not produce false positive reactions with 38 near-neighbor *B. cereus* group strains and detected all tested *B. anthracis* genotypes.

The assay sensitivity, as determined by dilution to extinction PCR using DNA from *B. anthracis* carrying both virulence plasmids, was approximately 500 pg, although greater sensitivity could be readily achieved by the use of nested primers, for example.

It is evident from the above results and discussion that the subject invention provides an important new means for the detection of *Bacillus* species and detection of *B. anthracis*. As such, the subject methods and systems find use in a variety of different applications, including research, medical, therapeutic, military and other applications. Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for detecting the presence or absence of a *B. anthracis* nucleic acid in a sample, comprising:

contacting a sample with first and second primers under nucleic acid amplification conditions, wherein:

i. the first primer binds to an insert sequence of an sspE gene, wherein said insert sequence comprises nucleotides 176-181 of SEQ ID NO:11; and ii. the second primer binds at a position that is separated from said insert sequence by at least 50 nucleotides, wherein a first amplification product is produced if *Bacillus* species nucleic acid is present in said sample and a second amplification product in addition to said first amplification product is produced only if *B. anthracis* nucleic acid is present in said sample, wherein said second amplification product is 117 nucleotides longer or shorter than said first amplification product; and assessing said amplification products to detect the presence or absence of said *B. anthracis* nucleic acid in said sample.

2. The method of claim 1, wherein said *B. anthracis* is a virulent, attenuated or non-virulent strain of *B. anthracis.*

3. The method of claim 1, wherein said method further comprises determining the virulence of said *B. anthracis.*

4. The method of claim 3, wherein said determining involves detecting amplification products from *B. anthracis* pXO1 or pXO2 plasmids.

5. The method of claim 1, wherein said assessing includes detecting the presence of an amplification product of a predefined size.

6. The method of claim 1, wherein said assessing is by real-time PCR.

* * * * *